(12) United States Patent
Zhang et al.

(10) Patent No.: US 10,174,123 B2
(45) Date of Patent: Jan. 8, 2019

(54) ANTIBODY AND BINDING FRAGMENT RECOGNIZING CACNA2D1 AND USE THEREOF

(75) Inventors: Zhiqian Zhang, Beijing (CN); Wei Zhao, Beijing (CN); Limin Wang, Beijing (CN); Haibo Han, Beijing (CN); Baocai Xing, Beijing (CN)

(73) Assignee: Beijing Institute for Cancer Research, Beijing (CN)

( * ) Notice: Subject to any disclaimer, the term of this patent is extended or adjusted under 35 U.S.C. 154(b) by 457 days.

(21) Appl. No.: 14/001,105

(22) PCT Filed: Feb. 22, 2012

(86) PCT No.: PCT/CN2012/000227
§ 371 (c)(1),
(2), (4) Date: Aug. 22, 2013

(87) PCT Pub. No.: WO2012/113266
PCT Pub. Date: Aug. 30, 2012

(65) Prior Publication Data
US 2014/0044729 A1   Feb. 13, 2014

(30) Foreign Application Priority Data
Feb. 22, 2011 (CN) .......................... 2011 1 0042166

(51) Int. Cl.
| | | |
|---|---|---|
| *C07K 16/30* | (2006.01) | |
| *C07K 16/28* | (2006.01) | |
| *C12N 5/20* | (2006.01) | |
| *C12N 5/10* | (2006.01) | |
| *C12N 15/85* | (2006.01) | |
| *A61K 39/00* | (2006.01) | |
| *A61K 39/395* | (2006.01) | |
| *A61K 45/06* | (2006.01) | |
| *C12Q 1/6886* | (2018.01) | |
| *G01N 33/574* | (2006.01) | |
| *G01N 33/68* | (2006.01) | |

(52) U.S. Cl.
CPC .......... *C07K 16/30* (2013.01); *A61K 39/0011* (2013.01); *A61K 39/39558* (2013.01); *A61K 45/06* (2013.01); *C12Q 1/6886* (2013.01); *G01N 33/574* (2013.01); *G01N 33/57492* (2013.01); *G01N 33/6872* (2013.01); *A61K 2039/505* (2013.01)

(58) Field of Classification Search
None
See application file for complete search history.

(56) References Cited

U.S. PATENT DOCUMENTS

2003/0044911 A1* 3/2003 Lerman ................. C07K 14/705
435/69.1
2003/0219861 A1* 11/2003 Rother ................... C07K 16/00
435/69.1
2006/0019256 A1* 1/2006 Clarke et al. ..................... 435/6
2009/0053232 A1* 2/2009 Eroglu ............... A61K 31/7105
424/139.1
2009/0148905 A1* 6/2009 Ashman ............... C07K 16/468
435/69.6
2010/0047782 A1* 2/2010 Cotterchio ........... C12Q 1/6886
435/6.12

FOREIGN PATENT DOCUMENTS

| CN | 102251013 A | 11/2011 |
| EP | 2192916 A1 | 6/2010 |
| WO | WO 01/20336 A2 | 3/2001 |
| WO | WO 2006/017293 A2 | 2/2006 |
| WO | WO 2009/029173 A1 | 3/2009 |

OTHER PUBLICATIONS

Paul, Fundamental Immunology, 3rd Edition, 1993, pp. 292-295.*
Bendig M. M. (Methods: A Companion to Methods in Enzymology, 1995; 8:83-93.*
Johnson and Wu (Methods in Molecular Biology, Antibody Engineering: Methods and Protocols, vol. 248, p. 11-25, 2004).*
Panka et Al. (Proceedings of the National Academy of Sciences USA, vol. 85, p. 3080-3084, 1988).*
MacCallum (J. Mol. Biol., 262, 732-745, 1996).*
Pascalis (The Journal of Immunology (2002) 169: 3076-3084).*
Vajdos (J. Mol. Biol. (2002) 320: 415-428).*
Portolano (The Journal of Immunology, vol. 150, No. 3, p. 880-887, 1993).*
Klimka (British Journal of Cancer (2000) 83: 252-260).*
Beiboer (J. Mol. Biol. (2000) 296:833-849).*
Rudikoff et al. (Proceedings of the National Academy of Sciences USA, vol. 79, p. 1979-1983, 1982).*
Harris (Biotechnology, vol. 11, p. 1293-1297, 1993).*
Colman P. M. (Research in Immunology, 145:33-36, 1994).*
Zhang (Cancer Research, vol. 71, No. 8, Abstract #1666, published Apr. 15, 2011).*
Xu, Xiaolan et al., Recurrent hepatocellular carcinoma cells with stem cell-like properties: possible targets for immunotherapy, Cytotherapy, 2010, vol. 12, pp. 190-200.
Du, Yantao et al., Twist Promotes Migration of Hepatocellular Carcinoma Cells, Chinese Journal of Clinical Oncology, 2010, No. 7, pp. 361-364.

(Continued)

*Primary Examiner* — Michael Allen
(74) *Attorney, Agent, or Firm* — Wolf, Greenfield & Sacks, P.C.

(57) ABSTRACT

Disclosed is a method for searching, identifying, or validating a marker CACNA2D1 of tumor-initiating cells. The method comprises a step of immunizing an animal using HEP-12 cells originating from a recurrent tumor and rich in originating cells. Also disclosed is a monoclonal antibody specially recognizing CACNA2D1 or antigen-binding fragments thereof, and the use thereof for treating or preventing tumors or diseases or conditions related to CACNA2D1.

12 Claims, 6 Drawing Sheets
Specification includes a Sequence Listing.

(56) References Cited

OTHER PUBLICATIONS

Extended European Search Report and Search Opinion dated Dec. 12, 2014 for EP Application No. 12749191.8.
International Search Report and Written Opinion dated May 31, 2012 for Application No. PCT/CN2012/000227.
Brown et al., Isolation of the [3H]gabapentin-binding protein/alpha 2 delta Ca2+ channel subunit from porcine brain: development of a radioligand binding assay for alpha 2 delta subunits using [3H]leucine. Anal Biochem. Jan. 15, 1998;255(2):236-43.
Munz et al., Side-by-side analysis of five clinically tested anti-EpCAM monoclonal antibodies. Cancer Cell Int. Nov. 2, 2010;10:44. doi: 10.1186/1475-2867-10-44.
Okamoto et al., Targeting cancer stem cells with monoclonal antibodies: a new perspective in cancer therapy and diagnosis. Expert Rev Mol Diagn. Jul. 2008;8(4):387-93. doi: 10.1586/14737159.8.4.387. Review.
Taylor et al., Immunostaining of rat brain, spinal cord, sensory neurons and skeletal muscle for calcium channel alpha2-delta (alpha2-delta) type 1 protein. Neuroscience. Aug. 13, 2008;155(2):510-21. doi:10.1016/j.neuroscience.2008.05.053. Epub Jun. 14, 2008.
Witcher et al., Characterization of the purified N-type Ca2+ channel and the cation sensitivity of omega-conotoxin GVIA binding. Neuropharmacology. Nov. 1993;32(11):1127-39.
Woodward et al., Cancer stem cells: markers or biomarkers? Cancer Metastasis Rev. Sep. 2008;27(3):459-70. doi: 10.1007/s10555-008-9130-2. Review.

\* cited by examiner

ANTIBODY AND BINDING FRAGMENT RECOGNIZING CACNA2D1 AND USE THEREOF

CROSS REFERENCE TO RELATED APPLICATIONS

This application is a U.S. National Phase filing of PCT/CN2012/000227, filed Feb. 22, 2012, which claims priority to Chinese Application No. 201110042166.6, filed Feb. 22, 2011, the entire contents of the aforementioned applications are hereby incorporated herein by reference.

TECHNICAL FIELD

The present invention relates to the field of pharmaceutical biotechnology. Specifically, the present invention relates to a method for seeking a marker of tumor initiating cells and/or a target molecule for tumor treatment, and also to a method for developing and screening a therapeutic drug that targets the marker of tumor initiating cells and/or the target molecule for tumor treatment. The present invention further relates to a monoclonal antibody or an antigen binding fragment thereof for tumor diagnosis, tumor prognosis and tumor treatment, a diagnostic kit or a pharmaceutical composition comprising the monoclonal antibody or the antigen binding fragment thereof, and the use of the monoclonal antibody or the antigen binding fragment thereof in the diagnosis, prognosis or treatment of tumors and the like. Further involved in the present invention is the use of the antigen targeted by the antibody or the target molecule recognized by the antibody in the diagnosis of tumors or the outcome prediction in cancer, the antigen or the target molecule being used as a marker of the tumor initiating cells (or referred to as tumor stein cells). In addition, the present invention discloses the use of the antigen targeted by the antibody or the target molecule recognized by the antibody as a molecular target in the development of reagents and drugs for tumor treatment.

BACKGROUND OF THE INVENTION

It is known for long that the tumor tissue consists of heterogeneous cell populations with different functions and morphologies. The tumor/cancer stem cells (TSC/CSC) hypothesis supposes that the tumor is formed via progressive proliferation and differentiation of tumor stem cells, which is similar to normal tissues and organs, leading to heterogeneity. The tumor stem cells, which are named for having properties similar to normal stem cells, refer to a group of cells that have a relatively low content in tumor tissues, infinite self-renewal ability and the ability of initiating tumor formation and growth. However, it does not mean that TSCs are definitely derived from corresponding normal stem cells or necessarily associated with normal stem cells. With this consideration, these cells are also called as tumor initiating cells (TIC) or tumor propagating cells (TPC) to avoid misunderstanding. Tumor stem cells exhibit strong tumorigenicity/carcinogenicity in animals (100 such cells, or even several such cells, may induce formation of tumor/cancer in immunodeficient mice), strong drug resistance and invasive growth. These cells also have a potential of differentiating into cells that are not tumorigenic. The presence of these tumor stem cells is regarded as the substantial cause of tumor generation, tumor development and treatment failure.

Since the tumor stem cells were isolated and identified from blood for the first time, tumor stem cells have been proved to be present in solid tumors such as brain cancer, breast cancer, prostatic cancer and colon cancer. Regarding liver cancer, several research groups employed different strategies and also found liver cancer stem cells derived from cultured cell lines or clinical specimens. For example, the side population (SP) cells isolated from Huh7 cells could induce tumors by animal experiments through continuous inoculation. Also, it is reported that CD133 can be used as a marker of liver cancer stem cells in Huh7 and PLC8024 cell lines. Recently, CD90, EpCAM, OV6, CD133/ALDH were also successfully used in separation of liver cancer stem cells. Although tumor cells with stem cell-like properties have been identified through different ways, various types of cells separated from tumors of different origins with a same marker differ greatly in biological properties as the already discovered markers of tumor stem cells did not exhibit a good specificity. In this regard, whether the tumor stem cells exist or not and what the tumor stem cells are in nature are being discussed. Actually, the term 'tumor stem cell' or 'tumor initiating cell', or even 'tumor propagating cell' is only an operational term, the nature of which needs to be further looked into. Nevertheless, a common conclusion is that, there are a group of cells in tumor tissues which are resistant to radiotherapy and chemotherapy and have strong tumorigenicity in immunodeficient animals. Whatever they are named as, they are the primary causes of treatment failure and tumor recurrence. Separation and identification of these cells provides a new idea to the diagnosis and treatment of tumors. Treatment in the past was mainly focused on low malignant cells which existed in a large quantity in the tumor popularity. However, the tumor initiating cells, despite of low percentage, would survive and gradually grow and transfer to other sites due to resistance to conventional radiotherapy and chemotherapy, leading to the recurrence and metastasis of tumors. In this regard, the drugs directed to eliminate tumor initiating cells can fundamentally prevent the tumors from recurring and metastasizing. These drugs, being alone or in combination with conventional surgeries, radiotherapy or chemotherapy will be the beginning of a new dawn for curing tumor completely. These tumor initiating cells should be treated as targets for tumor diagnosis, treatment and prognosis.

Recently, great progress has been achieved in experiments on tumor treatment by targeting the tumor stem cells. For example, in the colorectal cancer, the CD133-positive tumor stem cells express a high level of IL-4 and thus inhibit apoptosis, and thus, treating the CD133-positive tumor stem cells with inhibitors of IL-4 makes them more sensitive to drugs. Researches also indicated that the use of anti-CD44 antibody may eliminate the tumor stem cells in acute leucocythemia so as to cure such conditions.

The development of drugs against tumor stem cells may aim at key molecules in the signaling pathways involved in self-renewal, drug resistance or invasive growth of tumor stem cells. The drug development may also focus on markers located on the cell surface as well as the niches where the cells exist and live. Molecules involved in these key processes are found based on the isolation and identification of tumor stem cells and deep understanding of the nature of malignant biological properties as well as the underlying mechanism of regulation. It should be noted that, compared to the commonly mentioned tumor related antigens, molecules related to the tumor stem cells are usually expressed in a relatively low level. Thus, the discovery of these molecules is mainly based on the specific expression but not over-expression of these molecules in tumor stem cell-like populations.

With the current drug development technology advancing, a specific antagonist can be designed with respect to a specific molecule using computer simulation, and candidate drugs can be screened from existing libraries of lead drugs. Also, an antibody with antagonism effect can be prepared and target drugs can be screened out by using other molecular and cellular biotechnologies such as the phage display method.

Monoclonal antibody technology has been used as a conventional technology to prepare antibodies that targets specific antigens or particular cells. Many antibodies have been used directly or through modification via genetic engineering into chimeric mouse-human antibodies or even completely humanized antibodies to treat several clinical diseases such as therioma. So far, the experiments concerning the antibody-mediated tumor stein cell-targeted treatments involve CD44, p-glycoprotein 1, hyaluronan receptor, EpCAM, CD326, CXCR4, IL-4, DLL4, ALDH and etc.

A marker that may be used to specifically identify tumor initiating cells is needed in this field to screen and identify such cells. Furthermore, the marker can be used in the clinical diagnosis and prognosis. The marker can also be used in the study on the malignant biological behaviors of these cells and the molecular mechanism of regulation. In the meanwhile, drugs directed at the tumor initiating cells may be developed so as to treat tumors and prevent the tumors from recurring and metastasizing fundamentally.

SUMMARY OF THE INVENTION

One objective of the present invention is to seek, differentiate or identify a molecular target for isolation, identification and treatment of tumor initiating cells.

Another objective of the present invention is to provide a method for diagnosing, treating and preventing tumors or CACNA2D1 protein-related diseases or disorders.

The present invention provides a method for seeking, differentiating or identifying a marker of tumor initiating cells and/or a target/molecular target for tumor treatment, comprising a step of immunizing an animal using cells from recurrent tumor sources rich in tumor initiating cells.

The present invention further provides a method for diagnosis, treatment and prevention of tumors, comprising, adopting the method for seeking, differentiating or identifying a marker of tumor initiating cells and/or a target/molecular target for tumor treatment in the present invention, developing and/or screening an antibody or an antigen binding fragment, a single-stranded or double-stranded oligonucleotide, a nucleic acid, a short peptide or a small molecular compound agent thereof based on the marker and/or target/molecular target, wherein the antibody or the antigen binding fragment, the single-stranded or double-stranded oligonucleotide, the nucleic acid, the short peptide or the small molecular compound agent thereof reduces gene expression and/or protein activity of the marker or target/molecular target, or causes cytotoxic reaction after targeting the marker or the target/molecular target; and then administering a therapeutically effective amount of at least one of the antibody or the antigen binding fragment, the single-stranded or double-stranded oligonucleotide, the nucleic acid, the short peptide or the small molecular compound agent thereof to a subject in need.

The present invention further provides a monoclonal antibody or an antigen binding fragment thereof for diagnosis or treatment of tumors or CACNA2D1 protein-related diseases or disorders.

The present invention further provides the use of the monoclonal antibody or the antigen binding fragment thereof in the diagnosis, prognosis and treatment of tumors or CACNA2D1 protein-related diseases or disorders.

The inventors of the present invention have found that the voltage-dependent calcium-channel α2δ-1 subunit (referred to as CACNA2D1, GenBank NO. NM_000722.2) is a molecular marker of tumor initiating cells and a molecular target or target for tumor treatment. It is useful to develop diagnosis reagents and therapeutic drugs with respect to nucleic acids or proteins of CACNA2D1. The inventors of the present invention have established Hep-11 (originated from the primary hepatocellular carcinoma tissue) and Hep-12 (originated from recurrent hepatocellular carcinoma tissue) cell lines respectively from specimens of primary and recurrent lesions of a single HCC (hepatocellular carcinoma) patient. They also discovered that, based on the population and cloning analysis, most (over 80%) of the recurrent HCC tissue-derived Hep-12 cells were found to possess properties as tumor initiating cells while primary HCC tissue-derived Hep-11 cells were non-tumorigenic within 6 months following injection of up to $10^7$ cells. If Hep-12 cells were used to inoculate balb/c mice to prepare hybridomas, a specific antibody 1B50-1 can be obtained that specifically recognizes Hep-12 cells. The inventors found that, 100 to 1000 of 1B50-1 positive cells, which are sorted by flow cytometry from 5 liver cancer cell lines and 4 clinical specimens of liver cancer, were sufficient to initiate subcutaneous tumors in NOD/SCID mice. The gene expression and cell differentiation indicated that these antibody positive cells had properties as tumor initiating cells. Meanwhile, the inventors of the present invention found that if such antibodies were injected intraperitoneally into NOD/SCID mice bearing Hep-12 and Huh7 tumors, the transplanted tumors can be inhibited in a dose-dependent manner, wherein the inhibition ratio were respectively 80.4% and 65.5% (measured by weight, compared to the IgG control group). Immunoprecipitation and mass-spectrometry (MS) analysis showed that the antigen recognized by 1B50-1 was an ion channel protein of 150 kd. If the expression of the gene of the ion channel protein was inhibited by RNA interference, the growth of Hep-12 cells in nude mice can also be inhibited. All these results suggested that the antigen recognized by 1B50-1 was a novel marker of tumor initiating cells for liver cancer and also a molecular target for tumor treatment.

According to an embodiment of the present invention, the present invention provides a method for seeking, differentiating or identifying a marker of tumor initiating cells or a target/molecular target for tumor treatment. The present invention further provides a method for seeking, differentiating or identifying a molecular target that can be used in isolation, identification and treatment of tumor initiating cells. Said method comprises a step of immunizing an animal with cells from recurrent tumor sources rich in tumor initiating cells. In a specific, embodiment of the method for seeking a marker of tumor initiating cells and/or a target/molecular target for treatment of the present invention, the tumor can be liver cancer, colon cancer, rectal cancer, kidney cancer, esophagus cancer, gastric cancer, lung cancer, breast cancer, prostatic cancer or other tumors highly expressing genes of CACNA2D1. In another embodiment of the present invention, the tumor is liver cancer and the cells from recurrent tumor sources rich in tumor initiating cells are Hep-12 cells that are derived from recurrent liver cancer and are rich in tumor initiating cells. In the method for seeking a marker of tumor initiating cells and/or the target for treatment in the present invention, the method further comprises using Hep-12 and Hep-11 cells respectively derived from primary and recurrent liver cancer tissues of a single HCC patient as the cell pair for screening.

According to an embodiment of the present invention, the present invention provides a method for treating tumors, comprising 1) immunizing an animal (such as balb/c mice) using cells from recurrent tumor sources rich in tumor initiating cells (such as Hep-12 cells), and seeking, differentiating or indentifying a marker of tumor initiating cells and/or a target/molecular target for tumor treatment (such as CACNA2D1);

2) developing and/or screening an antibody or an antigen binding fragment, a single-stranded or double-stranded oligonucleotide, a nucleic acid, a short peptide or a small molecular compound agent thereof based on the marker and/or target/molecular target (such as CACNA2D1) as sought, differentiated or identified in step 1), wherein the antibody or the antigen binding fragment, the single-stranded or double-stranded oligonucleotide, the nucleic acid, the short peptide or the small molecular compound agent thereof reduces gene expression and/or protein activity of the marker or target/molecular target, or causes cytotoxic reaction after targeting the marker or the target/molecular target;

3) administering a therapeutically effective amount of at least one of the antibody or the antigen binding fragment, the single-stranded or double-stranded oligonucleotide, the nucleic acid, the short peptide or the small molecular compound agent thereof as developed or screened in step 2) to a subject in need.

According to an embodiment of the present invention, step 1) described above can be performed by immunizing animals (such as balb/c mice) with cells (such as Hep-12 cells) from recurrent tumor sources rich in tumor initiating cells so as to prepare hybridomas, obtaining a monoclonal antibody (such as 1B50-1). The cells (such, as Hep-12 cells) specifically recognized by the obtained antibody (such as 1B50-1) are used as candidate cells for differentiation and identification of tumor stem cells. Animal experiments (for example, whether 100 to 1000 cells can induce subcutaneous tumors in NOD/SCID mice), gene expression and cell differentiation and other studies are performed to determine whether the antibody positive cells possess properties of tumor stem cells. The antigens of the tumor stem cells specifically recognized by the monoclonal antibodies (such as 1B50-1) which are obtained by the method of the present invention are the marker of tumor initiating cells and/or target/molecular target for treatment that the present invention seeks for. According to a specific embodiment of the present invention, the inventors of the present invention have found CACNA2D1 protein and determined it as a marker of tumor initiating cells and/or a target/molecular target fore tumor/cancer treatment.

According to one embodiment of the present invention, the antibody or antigen binding fragment thereof as developed or screened in step 2) that reduces gene expression and/or protein activity of the marker, target or molecular target, or causes cytotoxic reaction after targeting the marker or target/molecular target can be a monoclonal antibody (such as 1B50-1) of the antigen (marker, target/molecular target for tumor/cancer treatment) as obtained in step 1) for seeking, differentiating or identifying tumor initiating cells, and they may also be other antibodies developed or screened out based on the sought, differentiated or identified marker, target/molecular target (such as CACNA2D1 protein/antigen).

Novel antibodies and derivatives thereof against the antigen CACNA2D1 can be obtained by various antibody preparation technologies based on the CACNA2D1, the antigen of tumor initiating cells as provided in the present invention. These technologies include, but are not limited to, expressing CACNA2D1 by various expression systems or purifying this antigen, and obtaining antiserum specific to the antigen by immunizing mice, rabbits or other animals (including genetically engineered animal strains); fusing spleen cells from immunized mice with SP2/0 myeloma cells, and then screening for monoclonal antibodies specific to the CACNA2D1 antigen by using CACNA2D1; further includes cloning the gene that codes the variable region of mouse anti-CACNA2D1 monoclonal antibody, then expressing a human-mouse chimeric antibody or monoclonal antibody in prokaryotic and/or eukaryotic expression system, directly or after humanization by correctly connecting the variable region to the coding gene of the constant region of corresponding humanized antibody. A fully human antibody specific to this gene can also be yielded by performing screening in the human antibody phage-displayed library by using CACNA2D1 or by chimera technology of fusing human peripheral blood mononuclear cells with mouse cells.

According to an embodiment of the present invention, the amount of CACNA2D1 protein can be quantified with a high sensitivity by using the antibody of the present invention. With the method for quantification of CACNA2D1 protein in vivo, the monoclonal antibody or antigen binding fragments thereof of the present invention can be used in the diagnosis of tumors or various CACNA2D1 protein-related diseases. Thus, the present invention further provides a method for diagnosing tumors or CACNA2D1 protein-related diseases or disorders, comprising administering an effective amount of at least one of the monoclonal antibody or antigen binding fragments thereof of the present invention to a subject in need. The dose required in the in vivo diagnosis may be lower than that is required in treatment, and can be determined by those skilled in the art through conventional procedures. The monoclonal antibody or antigen binding fragments thereof can also be used to specifically assay CACNA2D1 protein present in test liquids such as body fluids, tissues and etc.

According to an embodiment of the present invention, the present invention provides a monoclonal antibody or antigen binding fragments thereof that can specifically recognize the voltage-dependent calcium-channel α2δ-1 subunit (CACNA2D1). Said monoclonal antibody or the antigen binding fragments thereof that specifically recognize CACNA2D1 comprises:

(i) a heavy chain (referred to as H chain hereinafter), wherein the variable region of the heavy chain comprises complementarity determining regions (CDR) CDRH1 (SEQ NO. 1), CDRH2 (SEQ NO. 2) and CDRH3 (SEQ NO. 3); or (ii) a light chain (referred to as L chain hereinafter), wherein the variable region of the light chain comprises complementarity-determining regions CDRL1 (SEQ NO. 4), CDRL2 (SEQ NO. 5) and CDRL3 (SEQ NO. 6); or (iii) both (a) and (b).

In an embodiment of the present invention, the above monoclonal antibody or the antigen binding fragment thereof has one or more properties as follows: (1) it binds to CACNA2D1 protein; (2) the positive cells recognized by the monoclonal antibody or the antigen binding fragment thereof has properties as tumor initiating cells; (3) it inhibits the growth of CACNA2D1-expressing tumor cells in animals. The tumor as mentioned above can be liver cancer, colon cancer, rectal cancer, kidney cancer, esophagus cancer, gastric cancer, lung cancer, breast cancer, prostatic cancer or other tumors highly expressing genes of CACNA2D1.

In an embodiment provided in the present invention, the monoclonal antibody or the antigen binding fragment thereof of the present invention comprises a heave chain, and the variable region of the heavy chain comprises an amino acid sequence having at least 70%, 75%, 80%, 85%, 90%, 95% or 99% sequence identity with those of CDRH1, CDRH2 and CDRH3. In an embodiment provided in the present invention, the monoclonal antibody or the antigen binding fragment thereof of the present invention comprises a light chain, and the variable region of the light chain comprises an amino acid sequence having at least 70%, 75%, 80%, 85%, 90%, 95% or 99% sequence identity with those of CDRL1, CDRL2 and CDRL3. In an embodiment provided in the present invention, the antibody or the antigen binding fragment thereof may comprise both the heavy chain and light chain mentioned above. In another embodiment, the antibody or the antigen binding fragment thereof of the present invention may further comprise one or more CDRs having at least 70%, 75%, 80%, 85%, 90%, 95% or 99% sequence identity with any of the above CDRs or the combination thereof.

In an embodiment of the present invention, the present invention provides a monoclonal antibody or an antigen binding fragment thereof for the diagnosis, prognosis and treatment of tumors or CACNA2D1 protein-related diseases or disorders, comprising the monoclonal antibody or the antigen binding fragment thereof mentioned above. The above tumor or disease or disorder can be liver cancer, colon cancer, rectal cancer, kidney cancer, esophagus cancer, gastric cancer, lung cancer, breast cancer, prostatic cancer or other tumors highly expressing genes of CACNA2D1.

The present invention provides a hybridoma cell line, and this hybridoma cell line is a mouse hybridoma deposited in China General Microbiological Culture Collection Center (Institute of Microbiology Chinese Academy of Sciences, NO. 1 West Beichen Road, Chaoyang District, Beijing 100101, China) on Dec. 8, 2010 (CGMCC No. 4416)

In a specific embodiment of the present invention, the above monoclonal antibody is the monoclonal antibody 1B50-1 produced by the hybridoma cell line (CGMCC No. 4416).

In a further embodiment, the present invention further comprises, but not limited to, generating an antibody fragment that recognizes a specific epitope of the antigen based on the antibody mentioned above by well-known technologies. For example, immunoglobulin molecules can be subjected to proteolytic cleavage, using enzymes such as papain (to generate Fab fragment) or pepsin (to generate F(ab')$_2$ fragment), to generate Fab and F(ab')$_2$ fragments. F(ab')$_2$ fragment contains complete variable regions of the L and H chains, CH1 region and hinge region. Derivative sequences (e.g., using different signal peptides, or being modified by humanization based on bioinformatics analysis) can be further obtained based on the nucleotide or amino acid sequence of the antibody by using already-known public information (such as the information from Genbank, literatures or via conventional cloning and sequence analysis). Nucleic acids encoding said immunoglobulin can be chemically synthesized. Alternatively, the nucleic acids encoding the immunoglobulin can be obtained from proper resources (such as the cDNA library of the antibody, or nucleic acids isolated from any tissue or cells expressing this antibody such as the screened hybridoma expressing the antibody, preferably from a mRNA library or a cDNA library generated therefrom) by PCR amplification, using synthesized primers matching the sequences at 3' and 5' ends. The nucleic acids encoding the immunoglobulin can also be screened from, for example, a cDNA library by using oligonucleotide probes specific to particular gene sequences. Then, with any method known in the art, the nucleic acids produced by PCR amplification can be introduced into a replicable vector that can be expressed in different expression systems (prokaryotic and eukaryotic expression systems, cell-free translation system and so on), expressing genetically engineered antibody or the antigen binding fragment thereof having bioactivities similar to the antibody of the present invention.

In an embodiment provided in the present invention, the antibody or the antigen binding fragment thereof of the present invention can be produced by any other methods known in the art for synthesizing antibodies, such as recombinant expression or chemical synthesis.

The present invention also provides a pharmaceutical composition containing the monoclonal antibody or the antigen binding fragment thereof of the present invention. In a further embodiment of the present invention, this pharmaceutical composition may further contain a pharmaceutically acceptable carrier. In addition, the present invention provides a pharmaceutical composition for treatment of tumors or CACNA2D1 protein-related diseases or disorders, comprising the monoclonal antibody or the antigen binding fragment thereof of the present invention and a pharmaceutically acceptable carrier. In a specific embodiment of the present invention, the pharmaceutical composition of the present invention further comprises other active compounds that can additively or synergistically ameliorate said diseases or disorders. The active compounds include, but not limited to, other chemotherapy compounds and toxins for treating said diseases or disorders. The active compounds further include small molecule compounds and other antibodies or antigen binding fragments thereof. In specific, the above tumors or CACNA2D1 protein-related diseases or disorders can be liver cancer, colon cancer, rectal cancer, kidney cancer, esophagus cancer, gastric cancer, lung cancer, breast cancer, prostatic cancer or other tumors highly expressing genes of CACNA2D1.

Advantageously, the above pharmaceutical composition for oral or parenteral administration is prepared into a unit dosage form suitable for a proper and fixed dose of active components. Such unit dosage forms include, for instance, tablets, pills, capsules, injections, suppositories and etc.

According to an embodiment, the present invention provides a kit directed at genes or proteins of CACNA2D1. Wherein, the kit can be used to diagnose or treat or prevent tumors or CACNA2D1 protein-related diseases or disorders, and the kit may contain the monoclonal antibody or the antigen binding fragment thereof as mentioned above or nucleic acids such as DNA and mRNA directed at CACNA2D1. This kit can be used in the diagnosis, treatment or prevention of tumors such as liver cancer, colon cancer, rectal cancer, kidney cancer, esophagus cancer, gastric cancer, lung cancer, breast cancer, prostatic cancer or other tumors highly expressing genes of CACNA2D1. According to the knowledge of those skilled in the art, the antigen can be tested by methods such as quantitative RT-PCR in mRNA level, and the antigen can be tested with well-known technologies such as ELISA (enzyme-linked immuno sorbent assay), flow cytometry, immunohistochemistry (cytochemistry) using antibodies directed at this gene or small molecules specifically bond thereto. The specimens used can be derived from a patient's blood, tissues, exfoliated cells, and etc.

According to another embodiment, the present invention provides the use of the monoclonal antibody or the antigen binding fragment thereof as mentioned herein in the preparation of a drug for diagnosis, treatment or prevention of tumors or CACNA2D1 protein-related diseases or disorders. Said tumors or diseases or disorders can be liver cancer, colon cancer, rectal cancer, kidney cancer, esophagus cancer, gastric cancer, lung cancer, breast cancer, prostatic cancer or other tumors highly expressing genes of CACNA2D1. The monoclonal antibody or the antigen binding fragment thereof of the present invention can be used as a diagnostic agent for diagnosis of cancers (for example, whether tumor initiating cells are contained in a patient's tissues or serums, as well as prognosis and prediction of treatment sensitivity) and other CACNA2D1 protein-related diseases or disorders. The monoclonal antibody or the antigen binding fragment thereof of the present invention is capable of specifically recognizing the CACNA2D1 antigen and thus can be used to quantify the CACNA2D1 protein in test liquids, for example, by conventional methods of the art such as double antibody sandwich assay, competitive determination and immunoassay.

In another aspect, the present invention provides a method for treatment of tumors or CACNA2D1 protein-related diseases or disorders, comprising administering a therapeutically effective amount of at least one monoclonal antibody or the antigen binding fragment thereof of the present invention to a subject in need of such treatment.

In a further aspect, the present invention provides a method for preventing tumors or CACNA2D1 protein-related diseases or disorders, comprising administrating a prophylactically effective amount of at least one monoclonal antibody or the antigen binding fragment thereof of the present invention to a subject in need of such treatment.

For the above diagnosis, treatment and prevention methods, the monoclonal antibody or the antigen binding fragment thereof of the present invention can be used in combination with other agents enhancing the biological effects of the monoclonal antibody or the antigen binding fragment thereof. The examples of such agents for treatment include another kind of antibody, cytotoxins that inhibit cell growth or kill cells, radioactive elements and/or other therapeutic agents containing anti-inflammatory agent, antibiotics and etc.

The monoclonal antibody or the antigen binding fragment thereof of the present invention can be mixed in an appropriate solvent directly as a liquid preparation or prepared as a pharmaceutical composition in a proper dosage form to be administrated orally or parenterally.

The monoclonal antibody or the antigen binding fragment thereof of the present invention can be mixed with a pharmaceutically acceptable carrier, diluent, or excipient to prepare a pharmaceutical composition such that it is suitable for oral or parenteral administration. The monoclonal antibody or the antigen binding fragment thereof or the pharmaceutical composition of the present invention can be administrated by various known delivery systems such as liposome encapsulation, microparticles, microcapsules and etc. Administration methods include, but not limited to, intracutaneous, intramuscular, intraperitoneal, intravenous, subcutaneous, intranasal, epidural and oral administration. The compounds can be administrated in any way such as infusion or bolus infusion, or can be administrated by absorption via epithelium or mucosa (for example, oral mucosa or rectum, etc.). These compounds can be administrated together with other biologically active agents. The administration can be performed systematically or locally. Preferably, the monoclonal antibody or the antigen binding fragment thereof of the present invention is intravenously administrated. The monoclonal antibody of the present invention can also be locally administrated to areas in need of such treatment. The composition can be prepared by well-known methods and contains a carrier, a diluent or an excipient commonly used in the field of drug preparation. The examples of the carrier or excipient used in tablets include lactose, starch, sucrose, magnesium stearate and so on.

The injectable preparations may include dosage forms that may be used in intravenous injection, subcutaneous injection, intracutaneous injection and intramuscular injection as well as instillation. These injectable preparations can be prepared by well-known methods. The injectable preparations can be prepared by, for example, dissolving, suspending or emulsifying the above antibody or the salt thereof in a conventional sterile aqueous medium or oily medium for injection. The aqueous media for injection may be, for instance, a physiological saline, an isotonic solution containing glucose and other accessory ingredients. The medium can be used in combination with an appropriate solubilizer such as alcohols (such as ethanol), polyols (such as propylene glycol and polyethylene glycol), nonionic surfactants (such as Polysorbate 80) and etc. Suppositories for rectal administration can be prepared by mixing the above antibody or the salt thereof with conventional base materials for suppository.

According to an embodiment, the present invention further provides a method for preparing and screening drugs for the treatment of tumors or CACNA2D1 protein-related diseases or disorders, comprising developing and screening an antibody or an antigen binding fragment, a single-stranded or double-stranded oligonucleotide, a nucleic acid, a short peptide or a small molecular compound agent thereof with CACNA2D1 as the target, wherein the antibody or the antigen binding fragment, the single-stranded or double-stranded oligonucleotide, the nucleic acid, the short peptide or the small molecular compound agent thereof reduces gene expression and/or protein activity of CACNA2D1, or causes cytotoxic reaction after targeting said molecule.

Preferably, the above inventive scheme is mainly directed at the hepatocellular carcinoma, and gastric cancer, colon cancer, rectal cancer, kidney cancer, esophagus cancer, lung cancer, breast cancer, prostatic cancer or the like are also involved.

Furthermore, based on the CACNA2D1 antigen of tumor initiating cells as provided in the present invention, a small molecular compound inhibitor specific to that antigen can be easily obtained by computer simulation or screening from existing libraries of lead compounds.

According to a specific example of the present invention, interfering RNAs, ShRNA1 (SEQ NO. 7) and ShRNA2 (SEQ NO. 8), have been designed and synthesized for the genes of CACNA2D1, which are later loaded into a lentivirus expression vector. Such a lentivirus inhibits the expression of said gene and exhibits a significant inhibition effects on the growth of Hep-12 cells in immunodeficient animals. Based on the provided shRNA sequences, different single-stranded RNAs can be obtained by chemical synthesis and modification with the matching sequences as the core according to common knowledge of one skilled in the art. Alternatively, these core sequences can be carried in conventional vectors for genetic recombination with different promoters as well as cloning vectors.

Definitions

Some terms used in the present invention are defined as follows.

The terms 'tumor initiating cell', 'tumor stem cell' and 'tumor propagating cell' can be interchangeably used herein. These terms are used to refer to a type of cells in practical application and the biological properties of these cells have to be further studied. These cells generally have, but not limited to, the following properties: (1) highly malignant: a few cells (100 or even less) can induce tumors in immuno-deficient mice and such tumorigenicity is quite stable; (2) being resistant to conventional treatments: resistant or not sensitive to conventional radiotherapy and chemotherapy.

The term 'antibody' used in the present invention refers to an antibody molecule capable of specifically binding to target polypeptide or target sequence. This term also covers the complete antibody or the fragment thereof, including the antigen binding fragment thereof.

The 'antigen binding fragment thereof' used in the present invention refers to any antibody fragment that maintains the ability of specifically binding to target proteins, polypeptides or sequences, including single chain antibodies, Fab fragments, F(ab')$_2$ fragments, single chain antibodies (sFv) linked by disulfide bond(s), fragments containing either one of the light chain variable region (VL) and/or the heavy chain variable region or fragments containing CDR(s) that specifically binds to target proteins, polypeptides or sequences. Various methods for obtaining those antibody fragments are well known in the art.

The term 'complementarity determining region (CDR)' used in the present invention refers to a region of the antibody that recognizes and binds to the antigens, which contains specific amino acid sequence that directly determines the specificity of the antibody or the binding activity of the antibody to antigens.

The term 'specifically recognize' used in the present invention refers to the ability of the antibody or the antigen binding fragment thereof to specifically bind to target proteins, polypeptides or sequences. The antibody does not bind to other polypeptides or proteins non-specifically. Preferably, the antibody or the antigen binding fragment thereof that specifically recognizes the CACNA2D1 does not cross react with other antigens.

The term 'effective amount' used in the present invention refers to 'the therapeutically effective amount for inhibiting proliferation' or 'a prophylactically effective amount for inhibiting proliferation'. This term includes an amount effective, at dosages and for periods of time necessary, to achieve the desired result, e.g., sufficient to treat cell proliferation diseases. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

BRIEF DESCRIPTION OF THE DRAWINGS

FIG. 2 (A) shows the tumors formed in the NOD/SCID mice induced by 1B50-1 positive cells from different resources; FIG. 2 (B) shows the eosin-hematoxylin staining of tumors formed by 1B50-1 positive cells in NOD/SCID mice, indicating that the morphology of these tumors is similar to that of the tumor tissues in the patient who provides these 1B50-1 positive cells; FIG. 2 (C) shows the result of flow cytometry analysis, indicating that the purified 1B50-1 positive cells can differentiate into 1B50-1 positive and 1B50-1 negative cells; FIG. 2 (D) shows the result of the real-time fluorescence quantitative RT-PCR, suggesting that the 1B50-1 positive cells highly express several genes related to stem cells.

FIG. 3A shows the result of the immunoprecipitation analysis; and FIG. 3B shows the 1B50-1 negative cells transfected with a plasmid expressing CACNA2D1-myc, indicating that the Myc and 1B50-1 staining are co-localized on the cell membrane. The Merge panel shows the result when Myc staining and 1B50-1 staining are superposed.

FIG. 4(A) is a picture showing the representative immunohistochemistry staining result of 1B50-1 in cancer tissue, paracancerous tissue and a normal liver tissue. The arrows represent the positive cells. FIG. 4(B-E) show the Kaplan-Meier survival curves of 1B50-1 staining profiles in 86 pairs of liver cancer specimens, suggesting that the presence of 1B50-1 positive cells in paracancerous tissues at the incisal edge (C and E) but not in the liver cancer tissues (B and D) are negatively correlated with the disease-free survival after surgeries and the overall survival of the patient. FIG. 4(F) shows the multi-factor analysis result indicating the presence of 1B50-1 positive cells in paracancerous tissues at the incisal edge is an independent adverse factor for liver cancer prognosis. $^a$ Chi-square test. Abbreviations: 4y, four years; Ca, cancer tissue; CI, confidence interval; DFS, disease-free survival; OS, overall survival; PCa, paracancerous tissue; RR, relative risk.

FIG. 5A shows the RT-PCR analysis of CACNA2D1 gene expression in different cell lines; FIG. 5B shows the immunofluorescent staining of 1B50-1 in different cell lines.

FIG. 7A shows tumors induced by cells from different groups; FIG. 7B shows the growth curves of tumors from different groups in NOD/SCID mice; FIG. 7C shows the weights of tumors from different groups upon dissection; FIG. 7D shows the volumes of tumors from different groups upon dissection.

FIG. 8A shows tumors induced by cells from different groups; FIG. 8B shows the growth curves of cells from different groups in NOD/SCID mice; FIG. 8C shows the weights of tumors from different groups upon dissection; FIG. 8D shows the volumes of tumors from different groups upon dissection.

FIG. 9A shows the staining of 1B50-1 after RNA interference, suggesting significant reduction of cellular CACNA2D1s; FIG. 9B shows the growth curves of the tumors in animals following RNA interference; FIG. 9C shows the volumes of tumors upon dissection; FIG. 9D shows the weights of tumors upon dissection.

DETAILED DESCRIPTION OF THE INVENTION

Figure 1:
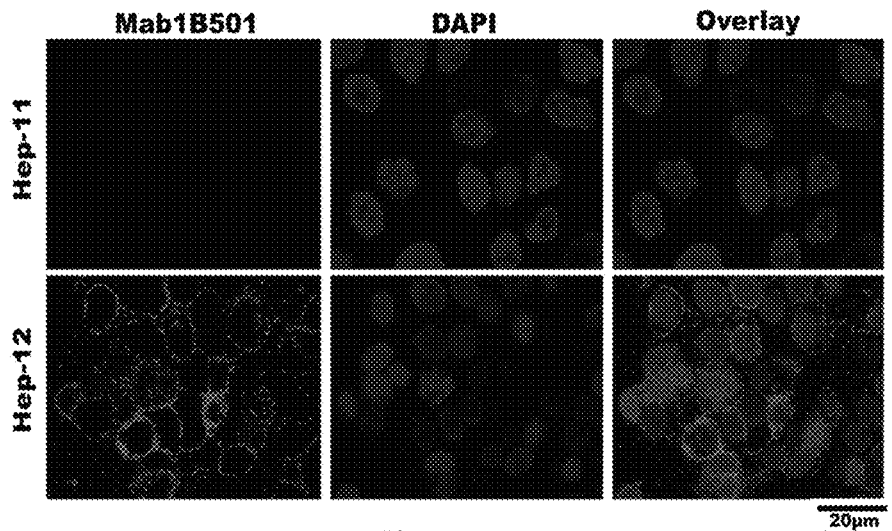
FIG. 1 shows the immunofluorescent staining of the antibody 1B50-1 in Hep-12 cells which are rich in liver cancer stem cells, indicating that the antigens recognized by 1b50-1 antibody are located on the cell membrane. Most Hep-12 cells are positive while most Hep-11 cells are negative.

The present invention will be further illustrated by providing the following examples. However, the present invention should not be limited to these examples.

The experimental methods used in the following examples are all conventional ones unless specifically indicated otherwise.

The materials and reagents used in the following examples are all commercially available unless specifically indicated otherwise.

Reagents and Materials

Cell lines Hep-11 and Hep-12 derived from primary and recurrent liver cancer tissues of a single patient were established by primary culture (see the detailed background about the cell pair in: Zhang Z, Xu X, Xing B, Wang Y, Han H, Zhao W. Identification and characterization of tumor-initiating cells with stem-like properties from a recurrent hepatocellular carcinoma [abstract], *Proceedings of the 100th Annual Meeting of the American Association for Cancer Research*, 2009 Apr. 18-22; Denver, Colo. Philadelphia (PA): *AACR*, 2009. Abstract nr 190; Xu X L, Xing B C, Han H B, Zhao W, Hu M H, Xu Z L, Li J Y, Xie Y, Gu J, Wang Y, Zhang Z Q. The properties of tumor-initiating cells from a hepatocellular carcinoma patient's primary and recurrent tumor, *Carcinogenesis*, 2010; 31(2):167-74.). The liver cancer cell lines HuH7 (Japan Society for the Promotion of Science), HepG2 (ATCC), SMMC-7721; breast cancer cell lines ZR-75 (ATCC), MCF-7 (ATCC), MDA-MB-231 (ATCC), BICR-H1 (donated by Professor Xinfu Huang from Beijing Cancer Hospital); lung cancer cell lines A549 (ATCC), Calu-3 (ATCC), Calu6 (ATCC), PG (donated by Professor Bingquan Wu from School of Basic Medical Sciences, Peking University); esophagus cancer cell lines KYSE150, KYSE510 (donated by Professor Fengmin Lu from School of Basic Medical Sciences, Peking University); gastric cancer cell lines BGC823, MGC803, SGC7901; prostatic cancer cell lines PC3M1E7, PC3M2B4 were common cell lines and are preserved in the laboratory of the present inventors.

The clinical tissue specimens were from the surgery resected specimens in Beijing Cancer Hospital and the pathological types were identified by pathology doctors.

Preparation of Hybridoma a) Mice immunization and cell fusion: Hep-11 and Hep-12 cells were used to immunize female Balb/C mice of 6-week old (from Vital River Laboratories Animal Technology Co., Ltd., Beijing) via subtractive immunization (Brooks, P. C., Lin, J. M., French, D. L., and Quigley, J. P. Subtractive immunization yields monoclonal antibodies that specifically inhibit metastasis. J Cell Biol, 1993, 122, 1351-1359; Rasmussen, N., and Ditzel, H. J. Scanning the cell surface proteome of cancer cells and identification of metastasis-associated proteins using a subtractive immunization strategy. J Proteome Res, 2009, 8:5048-5059). The Hep-11 cells with almost-saturated density were washed with PBS for three times and then the cells were collected by a cell scraper. These cells were suspended in sterile PBS ($\sim 5\times 10^6$ cells/ml) after centrifugation. Thereafter, female Balb/c mice of 4- to 6-week old were inoculated intraperitoneally with the prepared suspension, 0.5 ml per animal, 4 animals in total. Cyclophosphamide (Sigma-Aldrich, St Louis, Mo.) was injected intraperitoneally into mice (200 mg/kg body weight) at day 2 and day 4 after inoculation of Hep-11 cells. Hep-12 cells were prepared at day 18 by the same procedure as described above for Hep-11 cells. Each mouse was inoculated intraperitoneally with Hep-12 cells ($2.5\times 10^6$ cells/0.5 ml PBS). The immunization was enhanced every three weeks with the same amount of Hep-12 cells, three times in total. The spleens were separated three days after the last immunization enhancement so as to prepare a cell suspension. These cells were mixed with $10^8$ SP2/0 cells (ATCC). After being washed twice by serum-free RPMI1640 medium (Invitrogen), the mixed cells were allowed to fuse in 50% PEG4000 (Sigma-Aldrich) according to conventional protocols. The cells were re-suspended in 1640 Medium containing HAT (Sigma-Aldrich) and 15% of calf serum. Then, the cells were plated in a 96-well cell culture plate and were cultured in a $CO_2$ incubator. Five days later, the culture medium was replaced with new 1640 Medium containing HAT and 15% calf serums. About 2 weeks after cell fusion (depending on the growth of hybridoma), the supernatant was sampled to test and screen hybridoma clones that secrete specific antibodies.

b) Subclones were tested and screened from hybridoma clones: the Hep11 and Hep12 liver cancer cell lines in 1640 Medium containing 15% of calf serums were respectively plated onto a 96-well cell culture plate. After the cells adhered to the wall and converged, the supernatant was discarded and a pre-cooled PBS containing 0.125% glutaraldehyde was added. The plate was kept still for 5 minutes at room temperature and then the liquid was discarded. The cells were washed with PBS for three times. Then, PBS containing 5% of skimmed milk powders was added into the plate and the plate was blocked at 4° C. overnight. After the blocking solution was removed, the supernatant with cultured hybridoma clones was added and the plate was kept still at room temperature for one hour. The supernatant was removed and the plate was washed with PBS twice. The horse radish peroxidase-labeled goat-anti-mouse antibody was diluted with PBS containing 5% of skimmed milk powders and uniformly mixed. Then, the mixture was added into the 96-well cell culture plate and the plate was incubated for 1 hour at room temperature. Then, the supernatant was discarded and the plate was washed with PBS for 5 times. After the addition of substrate solution of ELISA, reaction was continued for 30 minutes away from light at room temperature until the addition of 12.5% sulphuric acid with an identical volume as the original solution to stop the reaction. The plate was placed into the ELISA reader to measure the optical density at 492 nm. The hybridoma clones negative to Hep11 and positive to Hep12 were picked and subcloned using limiting dilution methods. The stably-positive hybridoma clones after consecutive subcloning for three times were cultured to a larger extent and the obtained cells were stored in a frozen state.

More than 30 hybridoma cell strains were obtained after subcloning and identification, one of which was named for 1B50-1. This strain was deposited in China General Microbiological Culture Collection Center (CGMCC) on Dec. 8, 2010 with the deposit number of CGMCC No. 4416.

Preparation and Purification of Antibodies

After enlarged culture, the hybridoma clones secreting the specific antibody, 1B50-1, were inoculated intraperitoneally into female Balb/c mice pretreated with pristane (Sigma-Aldrich), $2 \times 10^6$ cells per mouse. The mice were sacrificed about one week later, and the ascites were taken for further test. Protein G affinity chromatography was conventionally performed to purify 1B50-1. The concentration of the purified 1B50-1 was calculated according the following equation: antibody (mg/ml)=$OD_{250} \times 0.6868$. The purity of the antibody was analyzed by using SDS-PAGE, and antibodies with their purity reaching electrophoresis grade were used for relevant experiments.

Determination of Subtypes of the Antibody

The subtypes of the antibody secreted from 1B50-1 hybridoma were determined according to the procedures recommended in the instruction of Mouse Monoclonal Antibody Isotyping Reagents (Cat# Iso2-1KT, Sigmal-Aldrich, St Louis, Mo., USA). The subtype-specific antibodies were diluted with PBS at a ratio of 1:1000 and then added into a 96-well test plate, 100 μL per well, two replicates. The plate was incubated for 1 hour at 37° C. and then washed with PBS for three times. Thereafter, the supernatant of 1B50-1 hybridoma was added and the plate was incubated for 1 hour until washing with PBS for three times. The horse radish peroxidase-labeled goat-anti-mouse antibody was diluted with PBS containing 5% of skimmed milk powders and then added into the test plate. The plate was incubated for 1 hour at room temperature and then washed with PBS for five times. After the addition of substrate solution of ELISA, reaction was continued for 30 minutes away from light at room temperature until the addition of 12.5% sulphuric acid with an identical volume as the original solution to stop the reaction.

According to the determination of the antibody 1B50-1, the reaction was strongly positive with subtype IgG3 while negative or weakly positive with other subtypes, suggesting that the antibody 1B50-1 belongs to subtype IgG3.

Cloning and Identification of Heavy Chain Variable Region and Light Chain Variable Region of the Antibody Total cellular RNA was extracted from 1B50-1 hybridoma cells by Trizol method and reverse-transcribed to cDNA using a reverse transcriptase Superscript III (Invitrogen). The heavy chain variable region and light chain variable region of 1B50-1 were respectively amplified by PCR using 5'-end degenerate primers for heavy chain variable region, 5'-CTTCCGGAATTCSARGTNMAGCTGSAGSAGTC-3' (SEQ ID NO: 7)+5'-CTTCCGGAATTCSARGT-NMAGCTGSAGSAGTCWGG-3' (SEQ ID NO: 8), 3'-end primer for heavy chain variable region 5'-GGAGGATCCA-GGGACCAAGGGATAGACAGATGG-3' (SEQ ID NO: 9), the forward primer for light chain variable region 5'-GGAGCTCGAYATTGTGMTSACMCARWCTMCA-3' (SEQ ID NO: 10) and the reverse primer for light chain variable region 5'-TATAGAGCTCAAGCTTGGATG-GTGGGAAGATGGATACAGTTGGTC-3' (SEQ ID NO: 11). The amplified product was cloned into a PCT-blunt vector (Invitrogen). The positive clones were selected and bi-directionally sequenced. Chothia standard domains (Morea V, Tramontano A, Rustici M, Chothia C, Leslc A M, Antibody structure, prediction and redesign. Biophys Chem. 1997 October; 68(1-3):9-16. Al-Lazikani B, Lesk A M, Chothia C. Standard conformations for the canonical structures of immunoglobulins. J Mol. Biol. 1997; 273(4):927-48.) were determined for the heavy chain and light chain based on the obtained amino acid sequence by tools provided in bioinf.org.uk/abs/chothia.html. In this way, the CDR sequences in the heavy chains and light chains were determined.

Construction and Expression of a Vector Expressing a Single Chain Antibody of Variable Regions of 1B50-1

To identify the cloned variable region, a vector was constructed to express a single chain antibody induced by the signal peptide MMP-3. This vector was used to transfect the QM-7 myoblasts. After induced differentiation, the medium was incubated with Hep-12 cells and then subjected to perform indirect immunofluorescent staining with MYC tagged-antibodies so that we can observe whether the transfected cells could specifically bind to Hep-12 cells.

Identification of Antigens recognized by 1B50-1

After removing the medium from cultures of Hep-11 and Hep-12 cells, the resultants were respectively added with supernatants of 1B50-1 hybridoma cultures. After incubation for 2 hours at 37° C. in an incubator, the culture media were discarded and the cells were washed with PBS for three times. The cells were harvested using a cell scraper and centrifuged. Then these cells were re-suspended in 5 ml of deionized water and subjected to ultrasonic processing. These cells were treated by ultrasonic waves again after addition of a 2× lysis solution. The solutions were centrifuged at 10000 rpm for 10 minutes at 4° C. The supernatants were taken and added to the Sepharose 4B-protein G (Pharmacia, Uppsala, Sweden) affinity chromatography column that has been equilibrated in advance. After being kept under room temperature for 1 hour, the column was purged with PBS. A 0.1M glycine-HCl buffer (pH2.5) was used to elute the bound antigens. The resultant solutions were adjusted to pH7.0 by adding 1M Tris-HCl (9.0). Then, a 2×SDS-PAGE sampling buffer was added in an identical amount to carry out SDS-PAGE analysis. After being stained by Coomassie brilliant blue 8250, the band that exhibited specific expression in Hep-12 cells and immunoprecipitated by 1B50-1 was cut out, which was used in MALDI-TOF-MS analysis after digestion with trypsins.

Reverse Transcription—PCR to Analyze the Gene Expression of CACNA2D1

After removal of culture medium, the cells with almost saturated density were washed with PBS and the total cellular RNA was extracted by Trizol methods. 3 μg of total cellular RNA was subjected to reverse transcription to synthesize the first strand cDNA in 20 μl of reaction system comprising, 1× reverse transcription buffer (50 mM Tris-HCl pH 8.3, 75 mM KCl and 3 mM MgCl.sub.2), 20 U of RNase inhibitor (Promega, Madison, Wis., USA), 10 mM DTT, 50 mM dNTP, 0.5 μg of oligo-$(dT)_{15}$ (Promega) and 200 U of Rodent Leukemia Virus Reverse Transcriptase (M-MLV-RT; Invitrogen). PCR was performed on 1 μL of cDNA with Taq DNA polymerase using forward primer: 5'-ACAGCAAGTGGAGTCAATCA-3' (SEQ ID NO: 12) and reverse primer: 5'-ACTGCTGCGTGCTGATAAG A-3' (SEQ ID NO: 13) for the gene of $CACNA_2D_1$. PCR was performed as follows: 94° C.×5 min (pre-denaturation); 94° C.×45 sec; 56° C.×45 sec; 72° C.×1 min, 25 cycles in total; 72° C.×10 min (extension). The product was subjected to agarose gel electrophoresis and then stained with ethidium bromide, and then the product was observed under ultraviolet light and photographed.

Real-time Fluorescence Quantitative RT-PCR Analysis cDNA was transcribed from the total cellular RNA by Rodent Leukemia Virus Reverse Transcriptase (M-MLV-RT; Invitrogen) and then realtime PCR amplification was performed in ABI7500 PCR system using SYBR Green PCR fluorescent dye mixture (Toyobo Co. Ltd., Osaka, Japan). The primers were listed in Table 1. The fold change of gene expression was calculated by $2^{-\Delta\Delta Ct}$ method (Pfaftl, M. W. A new mathematical model for relative quantification in real-time RT-PCR. Nucleic Acids Res 2001, 29: e45) with GAPDH being the internal control reference.

TABLE 1

Primers for PCR

| gene | Sense | SEQ ID NO: | Anti-sense | SEQ ID NO: |
|---|---|---|---|---|
| Sox2 | ACATGAACGGCTGGAGCAAC | 14 | AGGAAGAGGTAACCACAGGG | 15 |
| Oct-4 | GACAACAATGAAAATCTTCAGGAGA | 16 | CTGGCGCCGGTTACAGAACCA | 17 |
| Nanog | TGCCTCACACGGAGACTGTC | 18 | TGCTATTCTTCGGCCAGTTG | 19 |
| AFP | ACCATGAAGTGGGTGGAATC | 20 | TGGTAGCCAGGTCAGCTAAA | 21 |
| CEACAM6 | GAAATACAGAACCCAGCGAGTGC | 22 | CAGTGATGTTGGGGATAAAGAGC | 23 |
| CTTNB | TGATGGAGTTGGACATGGCC | 24 | CTCATACAGGACTTGGGAGG | 25 |
| KLF4 | AAGCCAAAGAGGGGAAGAC | 26 | CATCTGAGCGGGCGAATTTC | 27 |
| MDR-1 | GCCTGGCAGCTGGAAGACAAATAC | 28 | ATGGCCAAAATCACAAGGGTTAGC | 29 |
| ABCG2 | GGAGGCCTTGGGATACTTTGAA | 30 | GAGCTATAGAGGCCTGGGGATTAC | 31 |
| BMI1 | AGCAGCAATGACTGTGATGC | 32 | CAGTCTCAGGTATCAACCAG | 33 |
| GAPDH | GACCCCTTCATTGACCTCAAC | 34 | CTTCTCCATGGTGGTGAAGA | 35 |

Cloning of CACNA2D1 gene and Construction of Expression Vector

The $CACNA_2D_1$ gene (NM_000722.2; calcium channel, voltage-dependent, alpha 2/delta subunit 1) was divided into three parts according to the sequence described in Genebank and three pairs of primers were designed as follows:

```
Forward primer of Part 1:
                                            (SEQ ID NO: 36)
5'-CCGgaattcTATGGCTGCTGGCTGCCTGCTGG-3', Reverse primer of Part 1:
                                            (SEQ ID NO: 37)
5'-AACCATTAGGATCGATTGCAAAG-3';

Forward primer of Part 2:
                                            (SEQ ID NO: 38)
5'- TGTGTACCTGGATGCATTGGAACTG-3', Reverse primer of Part2:
                                            (SEQ ID NO: 39)
5'-ACCATCATCCAGAATCACACAATC-3';

Forward primer of Part 3:
                                            (SEQ ID NO: 40)
5'-AGAGACATATGAGGACAGCTTC-3', Reverse primer of Part 3:
                                            (SEQ ID NO: 41)
5'-GTCGACTACTTGTCATCGTCATCCTTGTAATCCTCGAGTAACAGGCG
GTGTGTGCTG-3'.
```

Three fragments covering the full length of the gene were amplified by PCR using the primers listed above with cDNA of Hep-12 cells as the template. The product was purified by agarose gel electrophresis and then introduced into the vector PCR-blunt for sequencing. The three fragments were cleaved by appropriate enzymes and connected by intermediate vector(s), finally obtaining the complete full-length gene $CACNA_2D_1$. The full-length $CACNA_2D_1$ gene was cloned into the vector pcDNA3.0-mychis (constructed by the present inventors based on pcDNA3.0 of Invitrogen).

Gene Transfection

The cells were inoculated and grew to a saturated density (80 to 90%) the next day. These cells were transfected with the constructed vector CACNA2D1 mychis/pcDNA3.0 via LIPOFECTAMINE 2000 (Invitrogen), a cationic lipid-based transfection reagent, according to the recommended protocol. The gene expression was analyzed by immunofluorescent staining cytochemistry 24 hours and 48 hours after the transfection.

Immunofluorescent Staining of Cells

The cultured cells were digested with trypsin: EDTA to prepare a single cell suspension. A suspension of $2 \times 10^6$ cells was taken and purified antibody 1B50-1 was added (diluted at a ratio of 1:100, the stocking liquid was 1 mg/ml). The mixture was incubated for 1 hour at 37° C. and washed with PBS for three times. Then, FITC-labeled goat-anti-mouse IgG secondary antibody (Jackson ImmunoResearch Laboratories, USA, 0.5 mg/ml; diluted at 1:100) was added and reacted for 1 hour. After being washed with PBS, the cells were observed under Leica SP5 confocal laser microscope or analyzed and sorted by Aria flow cytometer. The cells transfected with CACNA2D1 mychis/pcDNA3.0 were double stained with the monoclonal 1b50-1 and the rabbit polyclonal myc antibody. The rhodamine-labeled goat-anti-mouse IgG and FITC-labeled goat-anti-rabbit IgG were respectively used as the secondary antibodies.

Immunohistochemical Staining

The cryostat sections of clinical paracancerous tissues and liver cancer tissues were fixed with methanol for 30 seconds and then blocked with 5% of skimmed milk powders. The sections were incubated with the monoclonal antibody 1B50-1 (diluted at 1:100, containing 5% of BSA) overnight at 4° C. and then washed with PBS. After that, reaction was performed with FITC-labeled goat-anti-mouse IgG at room temperature for 2 hours. The sections were washed with PBS and the nucleoli were stained for 5 minutes with DAPI (1:2000). Sections were mounted using 2% DABCO in glycerol and observed under Leica SP5 confocal laser microscope.

Western Blot Analysis

The tissues or cultured cells were lysed in a Radio Immuno-precipitation assay buffer (Beijing Solarbio Science & Technology Co., Ltd) containing a mixture of 1 mM PMSF, complete protease inhibitor cocktail and phosphatase inhibitor cocktail (Roche, Mannheim, Germany). After electrophoresis in 10% SDS-PAGE, the proteins were transferred to an Immobilon-P® membrane (Millipore) (polyvinylidene fluoride microporous membrane). After the membrane was blocked with 5% of skimmed milk powders, the proteins were reacted with the primary antibody CACNA2D1 (Abcam, Cambridge, Mass.) or antibody specific to the internal reference .beta.-actin (Roche Applied Science) and then with HRP-labeled goat-anti-mouse secondary antibody (Jackson ImmunoResearch Laboratories Inc., West Grove, Pa., USA). The positive signals were detected by Immobilon™ Western Chemiluminescent HRP substrate (Millipore) through a chemical luminance method. The bands were scanned by a ChemiImager scanner (Alpha Innotech) for signals and the grey scales were quantified and analyzed using the software AlphaEaseFC. The relative amount of CACNA2D1 was calculated by using the grey scale of .beta.-actin as the internal reference.

Construction, Package and Infection of Lentivirus Vectors for RNA Interference to $CACNA_2D_1$ Gene The RNA sequence for interference of the $CACNA_2D_1$ gene was designed and synthesized by Origene. A retrovirus-based vector was constructed with a U6 promoter as the promoter, wherein sequence was ACTCAACTGGA-CAAGTGCCTTAGATGAAG (SEQ ID NO: 42) for nucleotides 546-574 in the coding sequence of CA CiVA2D1 and sequence 2 was AGATGCAAGAAGACCTTGTCA-CACTGGCA (SEQ ID NO: 43) for nucleotides 116-144 of the coding sequence. Nucleic acids with the same lengths randomly synthesized by Origene were used as the control sequences. The vectors bearing these sequences were cleaved by EcoR I and Sal I respectively and fragments containing the U6 promoter and these oligonucleotides were separated and purified via agarose gel electrophresis. The purified fragments were ligated with a Plenti6-linker vector (obtained by introducing an linker having multiple cloning sites into the plenti6 vector of Invitrogen cleaved by Cla and Age I, and stored in the inventors' laboratory) which had been cleaved by the same endonucleases. After determination, Lentiviral plasmid vectors plenti6U6CACNA2D1ShRNA-1, plenti6U6CACNA2D1ShRNA-2 and plenti6U6-control were obtained. The packaging of lentiviruses were performed in strict accordance with the recommended protocol provided by Invitrogen. The supernatant having lentiviruses particles were used to directly infect Hep-12 cells. Forty eight hours later, 6 μg/ml Blasticidin (Invitrogen) was added to screen cells infected by lentiviruses and the media were renewed every three days. In this way, cell populations infected by the above lentiviruses were obtained and Blasticidin contained in 6 μg/ml was continuously used during the whole experiment so that a screening pressure to the cells was maintained. The inhibitory effect on the gene $CACNA_2D_1$ was further observed in infected cells by RT-PCR and immunofluorescent cytochemistry staining. Also, the inhibitory effect on the tumor formation and growth was observed through tumorigenicity experiment in immunodeficient animals.

Tumor Initiation in Animals and Inhibitory Effect of Antibody on Tumors

Tumor Initiation Experiment: in the experiment for assaying the tumor initiation and self-renewal abilities of the tumor initiating cells, different amounts ($10^4$, $10^3$, $10^2$) of 1B50-1 positive or 1B50-1 negative cells derived from different resources and sorted by flow cytometry were mixed with BD Matrigel™ (BD Biosciences) (solubilized basement membrane preparation) (1:1) in identical volumes, and the mixture was used to inoculate NOD/SCID mice of 4 to 6-week old (Vital River Laboratories Animal Technology Co., Ltd., Beijing, SPF) subcutaneously (the antibody negative cells were inoculated on one side of a mouse and the antibody positive cells were inoculated on the other side of the same mouse). Each group consisted of 5 animals. The growth of tumors was observed every week. Then, in the experiment for observing the changes of tumor formation and tumor growth in animals after $CACNA_2D_1$ was inhibited, $2 \times 10^6$ cells were inoculated subcutaneously in NOD/SCID mice. When the tumors grew to a visible size, the major axis and minor axis of the tumors were measured every three days. The size of tumors can be calculated based on the equation that 'size of tumor=major axis×minor $axis_2$/2' and the data were used to draw the growth curve.

Inhibitory Effect of Antibody on Tumors: NOD/SCID mice of 4 to 6 weeks were inoculated with $2 \times 10^6$ liver cancer cells subcutaneously. When the tumors grew to a visible size (about 0.02-0.03 $cm^3$), animals were randomly divided into several groups, 6 animals per group. These animals were intraperitoneally injected every other day, respectively with PBS, control IgG (800 μg per animal, Zhongshan Golden Bridge Biotechnology) and 1B50-1 (respectively 200, 400 and 800 μg per animal). The major axis and minor axis were measured before each injection by vernier caliper, and the size of tumors was calculated based on the equation that 'size of tumor=major axis×minor $axis^2/2$'. After 7 administrations in total, the animals were sacrificed on the next day of the last administration. The tumors were dissected and wet weight and size were measured for those tumors.

Application Effect

Effect Example 1: 1B50-1 Recognized Antigens on the Membrane and the Positive Rate Differed Among Liver Cancer Cell Lines Hybridomas were prepared by subtractive immunization and screened via Hep-11 cells and Hep-12 cells. After three fusions, 37 monoclonal antibodies potentially specific to Hep-12 cells were obtained at the first round. These antibodies were subjected to further subcloning and preliminary analysis. One hybridoma was named for 1B50-1 which secreted antibodies located on the cell membrane (FIG. 1). The ratio of 1B50-1 positive cells was analyzed by flow cytometry in different liver cancer cell lines and cells originated primary culture of clinical specimens with liver cancer. The results were listed in Table 2. The Hep-12 cells from recurrent hepatocellular carcinoma rich in tumor initiating cells had a relatively high 1B50-1 positive rate while other cells had a low rate.

TABLE 2

The amount of 1B50-1 positive cells and the tumor initiation ability in NOD/SCID mice

| Cell | Percentage of 1B50-1+ cells# | 1B50-1 positive $10^3$ | 1B50-1 positive $10^2$ | 1B50-1 negative $10^3$ | 1B50-1 negative $10^2$ |
|---|---|---|---|---|---|
| HuH-7 | 0.9-2.2 | 5/5 | 5/5 | 3/5* | 0/5 |
| Hep-11 | 0.4-0.7 | 5/5 | 1/5 | 0/5 | 0/5 |
| Hep-12 | 92.1-94.8 | 5/5 | 5/5 | 3/5* | 0/5 |
| HepG2 | 0.5-2.1 | 4/5 | 4/5 | 0/5 | 0/5 |
| SMMC7721 | 0.5-0.6 | 5/5 | 5/5 | 0/5 | 0/5 |
| Case-1 | 1.7-3.3 | 5/5 | 5/5 | 3/5* | 0/5 |
| Case-2 | 0.6-2.1 | 3/5 | 2/5 | 0/5 | 0/5 |
| Case-3 | 0.4-1.8 | 5/5 | 3/5 | 5/5* | 1/5 |
| Case-4 | 0.6-1.3 | 2/5 | 0/5 | 0/5 | 0/5 | results based on 2-8 times of flow cytometry;
*the formed tumor was much smaller than the corresponding positive cells.

Figure 2:
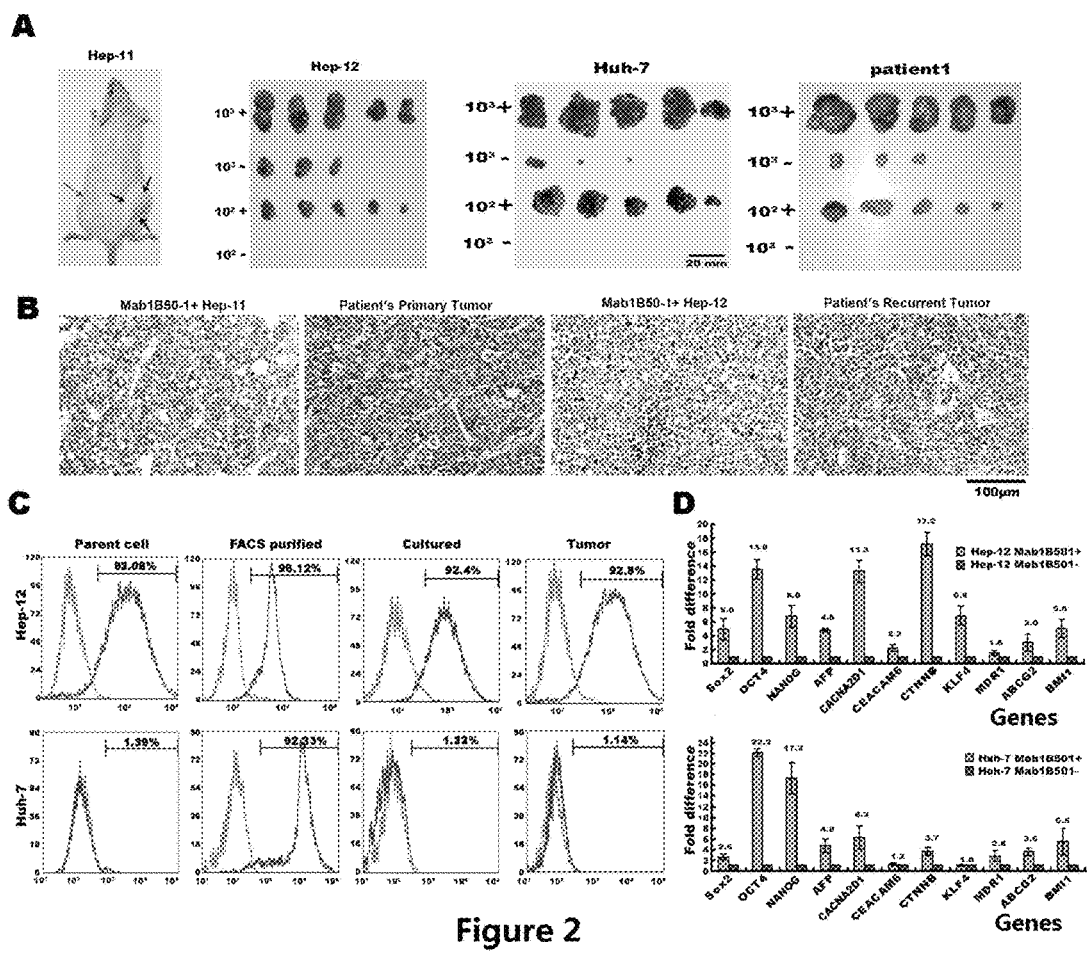
FIG. 2 shows the results of inoculation experiments in animals, which demonstrate that 1B50-1 positive cells have properties as the tumor initiating cells.

Effect Example 2: The Positive Cells Recognized by 1B50-1 had Properties as Tumor-Initiating Cells The 1B50-1 positive/negative cells were sorted by flow cytometer from five cell lines with hepatocellular carcinoma including Hep-11, Hep-12, HuH7, HepG2 and SMMC-7721. NOD/SCID mice were injected subcutaneously with 100 or 1000 selected cells (the antibody negative cells were inoculated on one side of a mouse and the antibody positive cells were inoculated on the other side of the same mouse). After 12-18 weeks, 100-1000 1B50-1-positive cells were sufficient to initiate subcutaneous tumors while negative cells did not grow or grew into small nodes (Table 2, FIG. 2), indicating that the 1B50-1 positive cells had properties as tumor initiating cells. The tumor initiation experiment using the 1B50-1 positive/negative cells sorted from primary culture of clinical liver cancer tissues resulted in similar results (Table 2). The 1B50-1 positive cells were sorted via flow cytometer from tumors induced by 1B50-1 positive HuH7 cells and then subcutaneously inoculated in NOD/SCID mice. It was found that 100% of these 1B50-1+ cells (5/5) were capable of forming tumors, suggesting that 1B50-1+ cells had the capacity of self-renewal. The expression of stem cell related genes in the 1B50-1 positive cells and negative cells were analyzed using realtime fluorescence quantitative RT-PCR. It was found that the stem cell related genes such as Nanog, Sox-2, AFP and ABCG2 were expressed at a high level in 1B50-1+ cells (FIG. D). The 1B50-1 positive cells were cultured in a medium containing 10% of fetal calf serum and the percentage of 1B50-1 positive cells was analyzed. It turned out that the percentage of 1B50-1+ cells decreased to the level measured in the parent cells (FIG. 2C), indicating that the 1B50-1 positive cells could differentiate into both 1B50-1 positive cells and 1B50-1 negative cells. These results suggested that the 1B50-1 positive cells had the properties as tumor-initiating cells.

Effect Example 3: The Antigen Recognized by 1B50-1 was CACNA2D1

Figure 3:
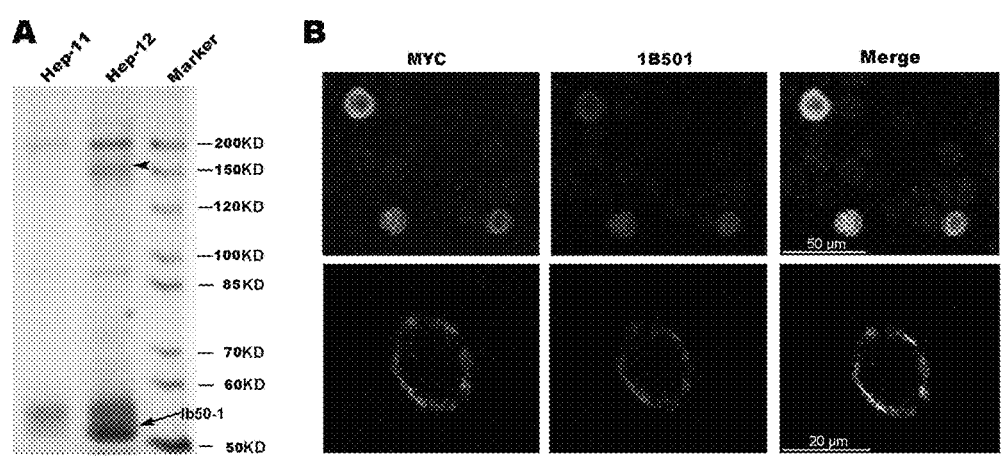
FIG. 3 shows the identification of CACNA2D1 recognized by 1B50-1.

A specific band of about 150 KD was obtained through immunoprecipitation by 1B50-1 in Hep-12 cells (the left panel of FIG. 3, the arrow indicated the band). MS analysis revealed that this protein was CACNA2D1. The corresponding gene was amplified by PCR using cDNA of Hep-12 cells as the template. By conventional DNA recombination, the amplified gene was added with the encoding sequence of a MYC tag peptide at its C terminal. Then, the gene was introduced into a eukaryocyte expression vector pcDNA3.0mychis, which is then transfected to cells that did not express such gene. Thereafter, the polyclonal MYC antibody and 1B50-1 were used to perform double staining. It turned out that the antibodies specific to MYC tags and 1B50-1 were consistently located on the cell surface of the transfected cells, indicating that the 1B50-1 did recognize CACNA2D1 (the right panel of FIG. 3).

Figure 4:
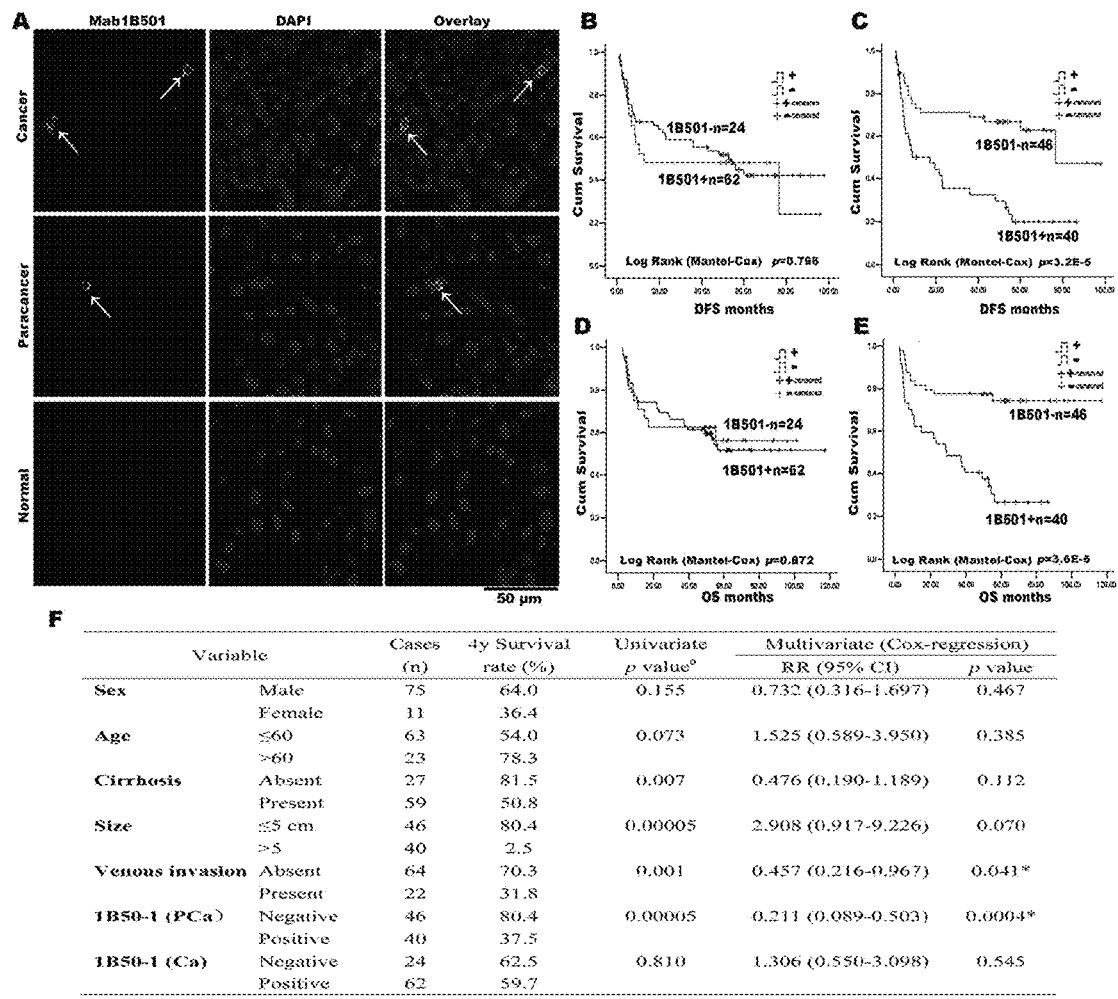
FIG. 4 shows the result of immunohistochemistry staining of 1B50-1 in the liver cancer specimens, indicating that the 1B50-1 positive cells are dispersed in the tumor tissue.

Effect Example 4: The Expression of the Gene CACNA2D1 in Clinical Liver Cancer Specimens Cryostat sections were obtained from cancers or paired paracancerous tissues of fresh specimens of clinical hepatocellular carcinom cases (86 patients in total). After fixation, these sections were stained with 1B50-1 via immunofluorecent histochemistry. The results were shown in FIG. 4 and Table 2. In 72.1% of these cases (62 cases/86 cases), the 1B50-1 positive cells were dispersed in the lesions (FIG. 4). The detection rate of positive cells in paracancerous tissues was 46.5% (40/86) which was lower than that in the cancer tissues. In 5 normal liver specimens (from resected specimens in haemangioma related surgeries), no 1B50-1 positive cells were detected to be present. In the cancer lesions and paracancerous tissues, the presence of 1B50-1 positive cells was statistically analyzed in combination with patients' clinical indices (Table 3). The presence of 1B50-1 positive cells in the cancer lesions was irrelevant to indices such as age, gender and occurrence of hepatocirrhosis. However, 1B50-1 positive cells in paracancerous tissues were positively correlated to the occurrence of hepatocirrhosis, survival of less than 4 years after surgery and recurrence within 2 years. The Kaplan-Meier curves and multivariate analysis using Cox's regression model showed that, the presence of 1B50-1 positive cells in paracancerous tissues of a patient with liver cancer predicted that the patient have worse disease-free survival and total survival after surgeries than those had 1B50-1 negative cells in paracancerous tissues (FIG. 4). As the paracancerous tissues were actually originated at the edge of removed cancer, whether 1B50-1 positive cells were present in paracancerous tissues can be used in prediction of the recurrence and prognosis in a patient. That is, the presence of 1B50-1 positive cells in paracancerous tissues can be used as HCC prognostic indicator.

TABLE 3

Correlation analysis between 1B50-1 staining and the clinical indications in liver cancer patients

| variable | Number of cases | 1B50-1 positive in paracancerous tissues [1] cases | 1B50-1 positive in paracancerous tissues [1] percentage | p value[2] | 1B50-1 positive in cancer tissues [1] cases | 1B50-1 positive in cancer tissues [1] percentage | P value[2] |
|---|---|---|---|---|---|---|---|
| Gender | | | | 0.223 | | | 0.960 |
| Male | 75 | 33 | 44 | | 54 | 72 | |
| Female | 11 | 7 | 63.6 | | 8 | 72.7 | |

TABLE 3-continued

Correlation analysis between 1B50-1 staining and the clinical indications in liver cancer patients

| variable | Number of cases | 1B50-1 positive in paracancerous tissues [1] | | | 1B50-1 positive in cancer tissues [1] | | |
|---|---|---|---|---|---|---|---|
| | | cases | percentage | p value[2] | cases | percentage | P value[2] |
| Age | | | | 0.733 | | | 0.063 |
| ≤60 | 63 | 30 | 47.6 | | 42 | 66.7 | |
| >60 | 23 | 10 | 43.5 | | 20 | 87.0 | |
| Hepatic cirrhosis | | | | 0.002 | | | 0.448 |
| No | 27 | 6 | 22.2 | | 18 | 66.7 | |
| Yes | 59 | 34 | 57.6 | | 44 | 74.6 | |
| Size of tumor | | | | 0.141 | | | 0.171 |
| ≤5 cm | 46 | 18 | 39.1 | | 36 | 78.3 | |
| >5 | 40 | 22 | 55 | | 26 | 65 | |
| Size of tumor | | | | 0.335 | | | 0.109 |
| ≤3 cm | 21 | 11 | 52.4 | | 18 | 85.7 | |
| >3 | 65 | 29 | 44.6 | | 44 | 67.7 | |
| Lymph vessel tumor emboli | | | | 0.170 | | | 0.635 |
| No | 64 | 27 | 42.2 | | 47 | 73.4 | |
| Yes | 22 | 13 | 59.1 | | 15 | 68.2 | |
| Survival | | | | 0.00005 | | | 0.810 |
| <4 years | 34 | 25 | 73.5 | | 25 | 73.5 | |
| ≥4 years | 52 | 15 | 28.8 | | 37 | 71.2 | |
| Recurrence | | | | 0.00004 | | | 0.893 |
| ≤2 years | 42 | 29 | 69.0 | | 30 | 71.4 | |
| ≥4 years | 44 | 11 | 25 | | 32 | 72.7 | |
| Total | 86 | 40 | 46.5 | | 62 | 72.1 | 0.0006* |

[1] A slice with one or more 1B50-1 staining positive cells was defined to be 1B50-1 positive.
[2] Chi-square test
*Tumor tissue group vs. paracancerous tissue group.

Figure 5:
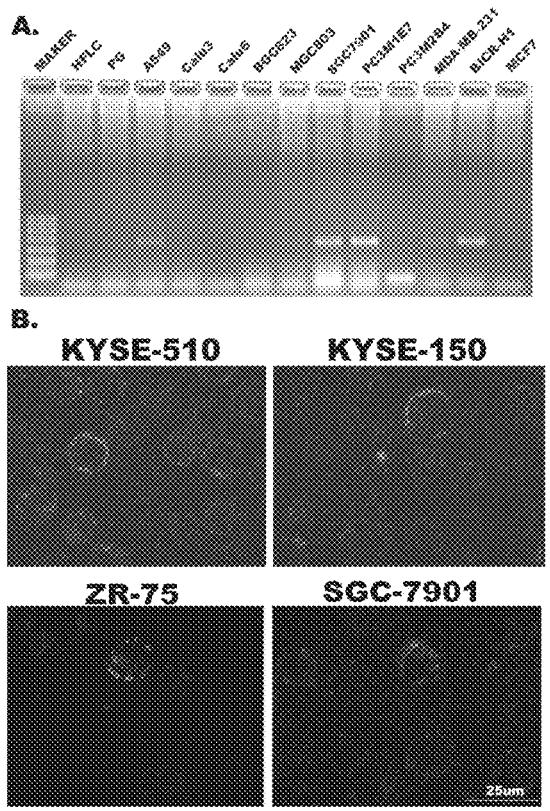
FIG. 5 shows the expression of CACNA2D1 gene in various tumor cell lines.

Effect Example 5. Expression of CACNA2D1 Gene in Cell Lines of Gastric Cancer, Esophagus Cancel; Breast Cancer, Lung Cancer The expression of CACANA2D1 gene in cell lines of common cancers besides liver cancer, such as gastric cancer, lung cancer, breast cancer and prostate cancer, was detected via RT-PCR. The results were shown in FIG. 5A. Positive bands were found in MGC-803 and SGC7901 among gastric cancer cells; PG and A549 among lung cancer cells; BICR-H1 and MDA-MB-231 among breast cancer cells. The gene was highly expressed in PC3M1E7 prostate cancer cells which are highly metastatic while no band was detected in PC3M2B4 cells that are lowly metastatic. The resulted revealed that, although not all the cells were positive, said gene was indeed positively expressed in partial cells for most cancers, exhibiting a similar result as observed in liver cancer cases. The above positive cells being highly metastatic suggested that said gene might be positively correlated to the metastasis of tumors. Furthermore, 1B50-1 was used in the immunofluorescent cytochemistry staining of some cells. It was found that CACNA2D1 was positively expressed in SGC7901 gastric cancer cells, KYSE-510 and KYSE-150 esophagus cancer cells and ZR-75 breast cancer cells, being located on the cell membranes. The number of positive cells greatly differed among different cell lines and the positive cells only accounted for a small percentage among all these cell lines (FIG. 5B). The results above were similar to what we had observed in the liver cancer, indicating that the discoveries in liver cancer might also be applicable to other tumors. That is, CACNA2D1 may possibly be used as molecular target for tumor diagnosis and tumor treatment.

Figure 6:
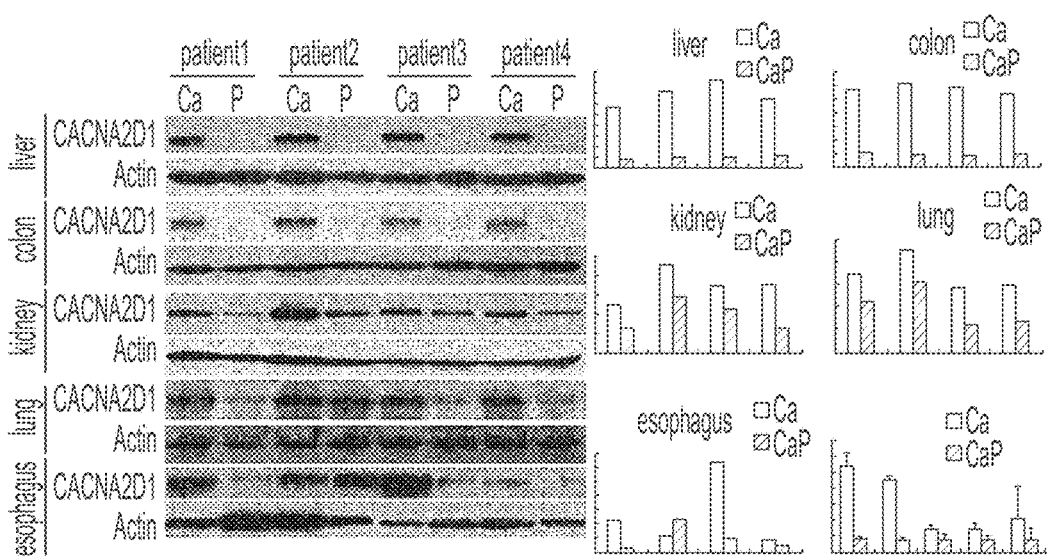
FIG. 6 shows analysis of CACNA2D1 expression in specimens of human tumor tissues (T) and normal paired paracancerous tissues (N). The left panel shows the result of Western blot and the right panel shows the quantitative result in which scanned grey scales of bands are calibrated using β-actin. Ca, cancer tissue; CaP, paracancerous tissue.
Figure 7:
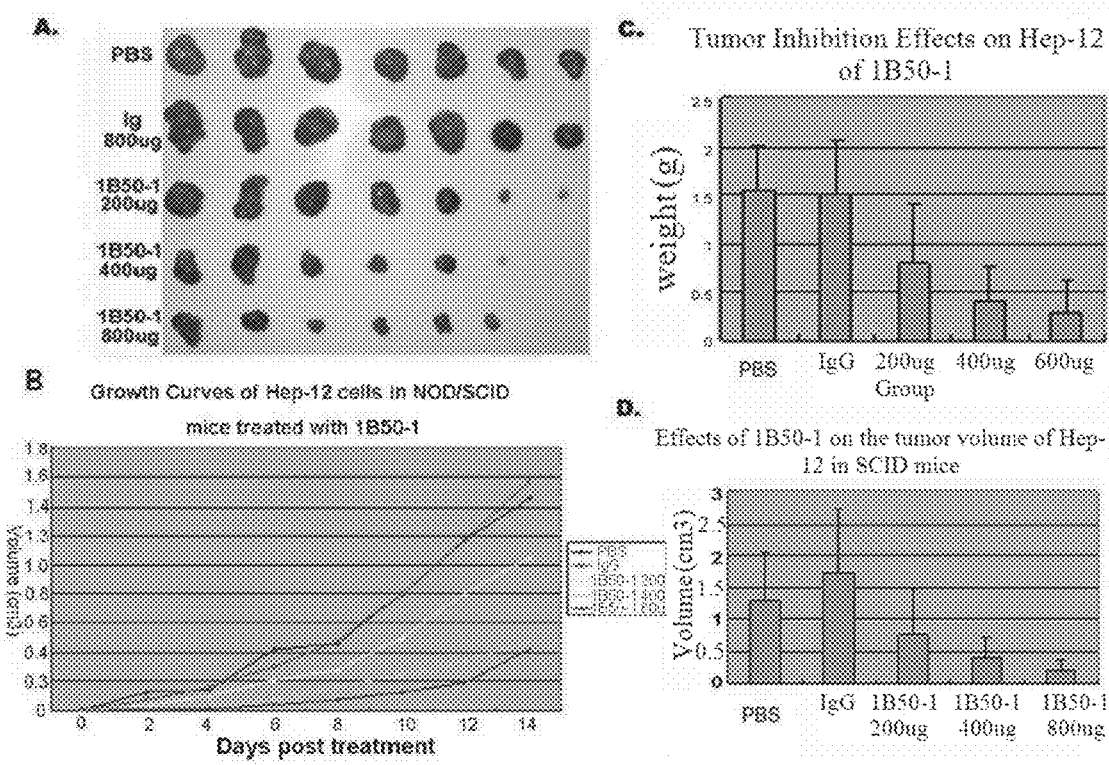
FIG. 7 shows the inhibitory effect of 1B50-1 antibody on the growth of transplanted tumors in NOD/SCID (non-obese diabetic/severe combined immune-deficient) mice induced by human Hep-12 cells.
Figure 8:
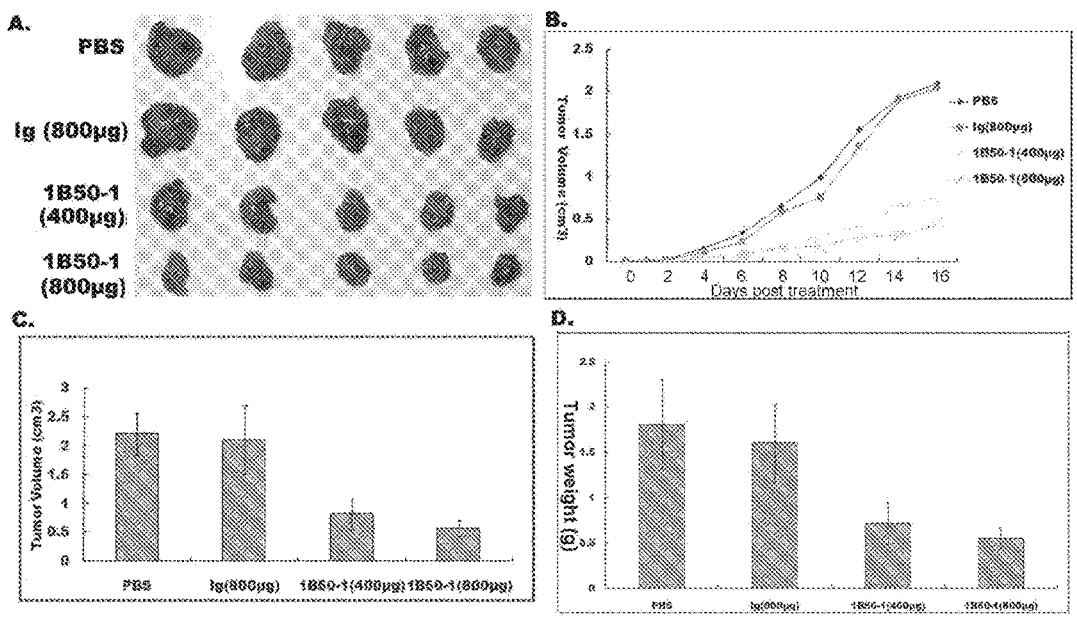
FIG. 8 shows the inhibitory effect of 1B50-1 antibody on the growth of transplanted tumors in NOD/SCID mice induced by human HuH7 cells.

Effect Example 6: Distribution of 1B50-1 Positive Cells in Other Tumor Tissue Specimens as Well Western Blot Analysis To further find out whether the conclusions obtained in the liver cancer tissues were also applicable to tumors of other types, immunohistochemistry staining was performed to clinical colorectal cancer, kidney cancer, lung cancer and esophagus cancer as well as their paired paracancerous tissues, 10 pairs for each type of cancer. The distribution of 1B50-1 positive cells was similar to that observed in liver cancer. The results were shown in Table 4. The cases having 1B50-1 positive cells in cancer tissues were more than those having 1B50-1 positive cells in paracancerous tissues. However, the cases were too few to have a statistic analysis. The results obtained in immunohistochemistry were further studied by performing western blot to clinical tissue specimens using commercially available antibody specific to CACNA2D1. As shown in FIG. 6, the expression of CACNA2D1 in some cancer tissues were clearly higher than that in paracancerous tissues (the expression level of CACNA2D1 differed among tumors of different types), indicating that the CACNA2D1 were expressed in a higher level when the cancer initiated. The high expression of CACNA2D1 existed in liver cancer as well as other cancers. Thus, drugs and molecular markers directed at CACNA2D1 could be used in cancers more than liver cancer.

TABLE 4

Detection of 1B50-1 positive cells in different tumor tissues and paracancerous tissues

| cancer | Total cases | number of cases with their cancer tissues detected as positive | number of cases with their paracancerous tissues detected as positive |
|---|---|---|---|
| Colorectal cancer | 10 | 8 | 3 |
| Lung cancer | 10 | 3 | 0 |
| Kidney cancer | 10 | 4 | 1 |
| Esophagus cancer | 10 | 1 | 0 |

Effect Example 7: The Inhibitory Effect of 1B50-1 on the Growth of Mice with Liver Cancer Bearing Tumors in the Liver Hep-12 and HuH7 liver cancer cells were respectively inoculated subcutaneously in immunodeficient animals. When the tumors grew to a size of 0.02-0.03 cm$^3$, 1B50-1 of different dosages was injected intraperitoneally into animals. As shown in the table and figure, tumor inhibition rates reached as high as 80.4% and 65.5% for Hep-12 and HuH-7 liver cancer cell lines (as measured by weight), respectively, in the 800 μg/mouse 1B50-1 treatment group. Such inhibition rates were dosage dependent and significantly statistically different from those in PBS control group and IgG treatment group.

Figure 9:
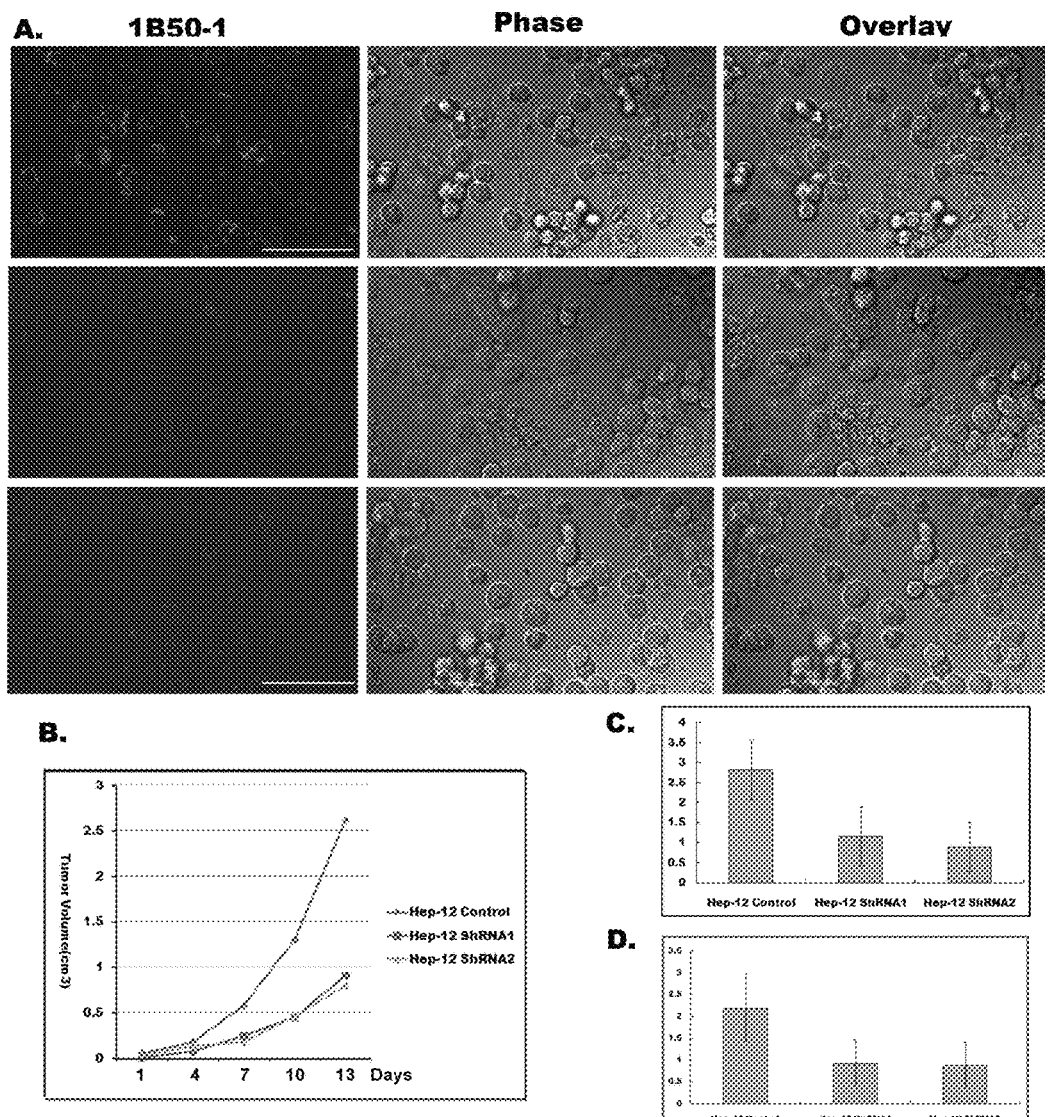
FIG. 9 shows the inhibition by RNA interference to CACNA2D1 gene on the growth of Hep-12 cells in NOD/SCID mice.

Effect Example 8: ShRNA Inhibited the Expression of CACNA2D1 in Hep-12 Cells and Further Prevented the Cells from Growing in the Animals To confirm whether the antigen CACNA2D1 recognized by 1B50-1 was a target molecule for tumor treatment, we constructed lentivirus vectors plenti6U6CACNA2D1shRNA-1 and plenti6U6CACNA2D1shRNA-2 that expressed RNA interfering CACNA2D1, and plenti6U6 as the control was enveloped into a lentivirus. These vectors were used to infect Hep-12 cells, and blasticidin (Invitrogen) was used to screen infected cells. The immunofluorescent cytochemistry staining of 1B50-1 (FIG. 9A) showed that the expression of CACNA2D1 was evidently suppressed when cells were infected by the two lentiviruses containing CACNA2D1 interfering RNA and quite rare positive fluorescence dots were found in the cell membrane. The fluorescence intensity was quite high in control group and the signals were found in most cells. Cell infected with lentiviruses as described above were inoculated into NOD/SCID mice subcutaneously, 2×10$^6$ cells per mouse and 5 mice per group. The formation of tumors was observed. As shown in FIG. 9B, cells infected by two lentiviruses carrying CACNA2D1 interfering RNA grew more slowly in animals than those with control vectors. The tumor inhibition rates were respectively 57.5% and 59.6% (measured by weight). The p values of t test were 0.0164 and 0.014 respectively as compared with the control group. These results suggested that inhibiting the expression of CACNA2D1 indeed suppressed the growth of Hep-12 cells in vivo. Thus, CACNA2D1 was a molecular target for tumor treatment.

Figure 10:
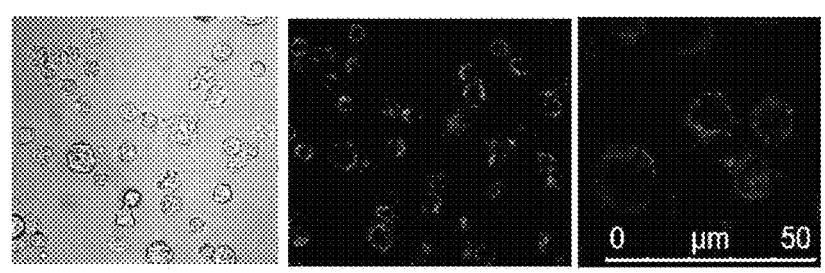
FIG. 10 shows that the single chain antibody expressed in QM-7 cells may bind to CACNA2D1 gene positive cells.

Effect Example 9: The Single Chain Antibody Expressed in Eukaryotic Cells could Recognize Hep-12 Cells The supernatant containing the single chain antibody of 1B50-1's variable regions expressed by QM-7 cells were incubated together with Hep-12 cells. The MYC-tagged 9E10 was used as the primary antibody and FITC-tagged goat-anti-mouse was used as the secondary antibody for staining. The staining was observed under the fluorescence microscope. Proteins on the cell surface of Hep-12 cells could be recognized by MYC-tagged 9E10 (FIG. 10). The fluorescent staining pattern was consistent as that with 1B50-1, suggesting that the expressed single chain antibody had a binding activity similar to that of 1B50-1. Also, this result further confirmed that the light chain variable region and heavy chain variable region of 1B50-1 were cloned with correct sequences. Further modification on antibody-drugs could be performed based on these sequences via genetic engineering.

Although specific embodiments of the present invention has been described, it will be appreciated by those skilled in the art that various changes and modifications may be made to these embodiments without departing from the principles or spirit of the present invention. Thus, the present invention intends to cover all these changes and modifications within the scope defined in the appended claims and their equivalents.

INDUSTRIAL APPLICATION

Markers of tumor initiating cells can be sought, differentiated or identified through the present invention. Also, the marker identified by the method of the present invention can be used in diagnosis, treatment and prevention of tumors. In specific, the present invention can be used to identify a maker specific to tumor initiating cells and the marker can be used to prepare therapeutic agents against tumor initiating cells and establish strategies for diagnosis, treatment and prognosis. All these may be helpful to solve the problems such as tumor recurrence and metastasis, providing a promising strategy for conquering tumor. Further, the monoclonal antibody or the monoclonal fragments thereof that specifically recognize CACNA2D1 as provided in this invention can be used directly in the treatment or prevention of tumors or CACNA2D1 protein-related diseases or disorders. Also, the monoclonal antibody or the monoclonal fragments thereof can be used in the preparation of pharmaceutical compositions and diagnostic kits.

We claim:

1. An antibody or an antigen binding fragment thereof comprising:
heavy chain complementarity determining regions CDRH1, CDRH2, and CDRH3 of 1B50-1 and light chain complementarity determining regions CDRL1, CDRL2, and CDRL3 of 1B50-1, wherein the CDRH1, CDRH2, CDRH3, CDRL1, CDRL2, and CDRL3 form an antigen binding site, wherein the heavy chain and light chain complementarity determining regions are determined by Chothia, and wherein 1B50-1 is the monoclonal antibody produced by hybridoma cell line Accession No. 4416 deposited with the China General Microbiological Culture Collection Center.

2. The antibody or the antigen binding fragment thereof of claim 1, wherein the antibody is the monoclonal antibody produced by hybridoma cell line Accession No. 4416 deposited with the China General Microbiological Culture Collection Center.

3. An isolated cell that produces the antibody or the antigen binding fragment thereof of claim 1.

4. A composition comprising the antibody or the antigen binding fragment thereof of claim 1, wherein the composition further comprises an additional reagent.

5. An isolated nucleic acid molecule comprising a polynucleotide that encodes the antibody or the antigen binding fragment thereof of claim 1.

6. The isolated nucleic acid molecule of claim 5, wherein the polynucleotide encodes the antigen binding fragment of the antibody.

7. A kit comprising the antibody or the antigen binding fragment thereof of claim 1 and at least one agent for detecting the binding or absence of binding of the antibody or antigen binding fragment thereof of claim 1 to CACNA2D1.

8. The kit of claim 7, wherein the kit comprises the antigen binding fragment of claim 1.

9. The antibody or the antigen binding fragment thereof of claim 1, wherein the antibody is a monoclonal antibody.

10. The antibody or the antigen binding fragment thereof of claim 1, wherein the antigen binding fragment is an antigen binding fragment of 1B50-1.

11. A pharmaceutical composition comprising the antibody or antigen binding fragment thereof of claim 1 and a pharmaceutically acceptable carrier.

12. The antibody or the antigen binding fragment thereof of claim 1, wherein the antibody or antigen binding fragment thereof binds CACNA2D1 on a tumor cell.

* * * * *

SEQUENCE LISTING

<160> NUMBER OF SEQ ID NOS: 43

<210> SEQ ID NO 1
<211> LENGTH: 7
<212> TYPE: PRT
<213> ORGANISM: Mus musculus
<220> FEATURE:
<221> NAME/KEY: MISC_FEATURE -continued

```
<222> LOCATION: (1)..(7)
<223> OTHER INFORMATION: complementarity determining region 1 of the
      heavy chain

<400> SEQUENCE: 1

Thr Ser Gly Met Gly Val Ser
1               5

<210> SEQ ID NO 2
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: complementarity determining region 2 of the
      heavy chain

<400> SEQUENCE: 2

Gln Ile Tyr Trp Asp Asp Lys Arg Tyr Asp Pro Ser Leu Lys Ser
1               5                   10                  15

<210> SEQ ID NO 3
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: complementarity determining region 3 of the
      heavy chain

<400> SEQUENCE: 3

Arg Gly Thr Gly Thr Pro Phe Asp Tyr
1               5

<210> SEQ ID NO 4
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: Complementary determining region 1 of the light
      chain of the antibody

<400> SEQUENCE: 4

Arg Ala Ser Gln Ser Ile Gly Thr Ser Ile His
1               5                   10

<210> SEQ ID NO 5
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Complementarity determining region 2 of the
      light chain

<400> SEQUENCE: 5

Tyr Ala Ser Asp Ser Ile Ser
1               5

<210> SEQ ID NO 6
<211> LENGTH: 8
<212> TYPE: PRT
<213> ORGANISM: Mus musculus
<220> FEATURE:
```

```
<221> NAME/KEY: MISC_FEATURE
<222> LOCATION: (1)..(8)
<223> OTHER INFORMATION: Complementarity determining region 3 of the
      light chain

<400> SEQUENCE: 6

Leu Gln Thr Asn Ser Trp Pro Trp
1               5

<210> SEQ ID NO 7
<211> LENGTH: 32
<212> TYPE: DNA
<213> ORGANISM: Mus musculus
<220> FEATURE:
<221> NAME/KEY: primer_bind
<222> LOCATION: (1)..(32)
<223> OTHER INFORMATION: 5 prime end degenerate primer 1 for heavy chain
      variable region
<220> FEATURE:
<221> NAME/KEY: misc_feature
<222> LOCATION: (18)..(18)
<223> OTHER INFORMATION: n is a, c, g, or t

<400> SEQUENCE: 7
cttccggaat tcsargtnma gctgsagsag tc                                     32

<210> SEQ ID NO 8
<211> LENGTH: 35
<212> TYPE: DNA
<213> ORGANISM: Mus musculus
<220> FEATURE:
<221> NAME/KEY: primer_bind
<222> LOCATION: (1)..(35)
<223> OTHER INFORMATION: 5 prime end degenerate primer 2 for heavy chain
      variable region
<220> FEATURE:
<221> NAME/KEY: misc_feature
<222> LOCATION: (18)..(18)
<223> OTHER INFORMATION: n is a, c, g, or t

<400> SEQUENCE: 8
cttccggaat tcsargtnma gctgsagsag tcwgg                                  35

<210> SEQ ID NO 9
<211> LENGTH: 33
<212> TYPE: DNA
<213> ORGANISM: Mus musculus
<220> FEATURE:
<221> NAME/KEY: primer_bind
<222> LOCATION: (1)..(33)
<223> OTHER INFORMATION: 3 prime end degenerate primer for Ig heavy
      chain variable region

<400> SEQUENCE: 9
ggaggatcca gggaccaagg gatagacaga tgg                                    33

<210> SEQ ID NO 10
<211> LENGTH: 31
<212> TYPE: DNA
<213> ORGANISM: Mus musculus
<220> FEATURE:
<221> NAME/KEY: primer_bind
<222> LOCATION: (1)..(31)
<223> OTHER INFORMATION: forward primer for Ig light chain variable
      region

<400> SEQUENCE: 10
ggagctcgay attgtgmtsa cmcarwctmc a                                      31
```

-continued

<210> SEQ ID NO 11
<211> LENGTH: 45
<212> TYPE: DNA
<213> ORGANISM: Mus musculus
<220> FEATURE:
<221> NAME/KEY: primer_bind
<222> LOCATION: (1)..(45)
<223> OTHER INFORMATION: reverse primer for Ig light chain variable
      region

<400> SEQUENCE: 11
tatagagctc aagcttggat ggtgggaaga tggatacagt tggtc                45

<210> SEQ ID NO 12
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: CACNA2D1forward primer for qRT PCR

<400> SEQUENCE: 12
acagcaagtg gagtcaatca                                            20

<210> SEQ ID NO 13
<211> LENGTH: 19
<212> TYPE: DNA
<213> ORGANISM: Homo sapiens
<220> FEATURE:
<221> NAME/KEY: primer_bind
<222> LOCATION: (1)..(19)
<223> OTHER INFORMATION: CACNA2D1 reverse primer for qRT PCR

<400> SEQUENCE: 13
actgctgcgt gctgataag                                             19

<210> SEQ ID NO 14
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: SOX2 sense primer for qRT PCR

<400> SEQUENCE: 14
acatgaacgg ctggagcaac                                            20

<210> SEQ ID NO 15
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: SOX2 antisense primer for qRT PCR

<400> SEQUENCE: 15
aggaagaggt aaccacaggg                                            20

<210> SEQ ID NO 16
<211> LENGTH: 25
<212> TYPE: DNA
<213> ORGANISM: Homo sapiens
<220> FEATURE:
<221> NAME/KEY: primer_bind
<222> LOCATION: (1)..(25)
<223> OTHER INFORMATION: OCT4 sense primer for qRT PCR

```
<400> SEQUENCE: 16
gacaacaatg aaaatcttca ggaga                                           25

<210> SEQ ID NO 17
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: OCT4 antisense primer for qRT PCR

<400> SEQUENCE: 17
ctggcgccgg ttacagaacc a                                               21

<210> SEQ ID NO 18
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: NANOG sense primer for qRT PCR

<400> SEQUENCE: 18
tgcctcacac ggagactgtc                                                 20

<210> SEQ ID NO 19
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: NANOG anti-sense primer for qRT PCR

<400> SEQUENCE: 19
tgctattctt cggccagttg                                                 20

<210> SEQ ID NO 20
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: AFP sense primer for qRT PCR

<400> SEQUENCE: 20
accatgaagt gggtggaatc                                                 20

<210> SEQ ID NO 21
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: AFP anti-sense primer for qRT PCR

<400> SEQUENCE: 21
tggtagccag gtcagctaaa                                                 20

<210> SEQ ID NO 22
<211> LENGTH: 23
<212> TYPE: DNA
```

```
<213> ORGANISM: Homo sapiens
<220> FEATURE:
<221> NAME/KEY: primer_bind
<222> LOCATION: (1)..(23)
<223> OTHER INFORMATION: CEACAM6 sense primer for qRT PCR

<400> SEQUENCE: 22
gaaatacaga acccagcgag tgc                                    23

<210> SEQ ID NO 23
<211> LENGTH: 23
<212> TYPE: DNA
<213> ORGANISM: Homo sapiens
<220> FEATURE:
<221> NAME/KEY: primer_bind
<222> LOCATION: (1)..(23)
<223> OTHER INFORMATION: CEACAM6 anti-sense primer for qRT PCR

<400> SEQUENCE: 23
cagtgatgtt ggggataaag agc                                    23

<210> SEQ ID NO 24
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: CTNNB sense primer for qRT PCR

<400> SEQUENCE: 24
tgatggagtt ggacatggcc                                        20

<210> SEQ ID NO 25
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: CTNNB antisense primer for qRT PCR

<400> SEQUENCE: 25
ctcatacagg acttgggagg                                        20

<210> SEQ ID NO 26
<211> LENGTH: 19
<212> TYPE: DNA
<213> ORGANISM: Homo sapiens
<220> FEATURE:
<221> NAME/KEY: primer_bind
<222> LOCATION: (1)..(19)
<223> OTHER INFORMATION: KLF4 sense primer for qRT PCR

<400> SEQUENCE: 26
aagccaaaga ggggaagac                                         19

<210> SEQ ID NO 27
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: KLF4 antisense primer for qRT PCR

<400> SEQUENCE: 27
catctgagcg ggcgaatttc                                        20
```

<210> SEQ ID NO 28
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: MDR1 sense primer for qRT PCR

<400> SEQUENCE: 28
gcctggcagc tggaagacaa atac                                          24

<210> SEQ ID NO 29
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: MDR1 antisense primer for qRT PCR

<400> SEQUENCE: 29
atggccaaaa tcacaagggt tagc                                          24

<210> SEQ ID NO 30
<211> LENGTH: 22
<212> TYPE: DNA
<213> ORGANISM: Homo sapiens
<220> FEATURE:
<221> NAME/KEY: primer_bind
<222> LOCATION: (1)..(22)
<223> OTHER INFORMATION: ABCG2 sense primer for qRT PCR

<400> SEQUENCE: 30
ggaggccttg ggatactttg aa                                            22

<210> SEQ ID NO 31
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: ABCG2 antisense primer for qRT PCR

<400> SEQUENCE: 31
gagctataga ggcctgggga ttac                                          24

<210> SEQ ID NO 32
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: BMII sense primer for qRT PCR

<400> SEQUENCE: 32
agcagcaatg actgtgatgc                                               20

<210> SEQ ID NO 33
<211> LENGTH: 20
<212> TYPE: DNA
<213> ORGANISM: Homo sapiens
<220> FEATURE:
<221> NAME/KEY: primer_bind
<222> LOCATION: (1)..(20)

<223> OTHER INFORMATION: BMI1 antisense primer for qRT PCR

<400> SEQUENCE: 33
cagtctcagg tatcaaccag                                           20

<210> SEQ ID NO 34
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: GAPDH sense primer for qRT PCR

<400> SEQUENCE: 34 gacccccttca ttgacctcaa c                                        21

<210> SEQ ID NO 35
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: GAPDH antisense primer for qRT PCR

<400> SEQUENCE: 35
cttctccatg gtggtgaaga                                           20

<210> SEQ ID NO 36
<211> LENGTH: 32
<212> TYPE: DNA
<213> ORGANISM: Homo sapiens
<220> FEATURE:
<221> NAME/KEY: primer_bind
<222> LOCATION: (1)..(32)
<223> OTHER INFORMATION: Cloning forward primer of CACNA2D1 part 1

<400> SEQUENCE: 36
ccggaattct atggctgctg gctgcctgct gg                             32

<210> SEQ ID NO 37
<211> LENGTH: 23
<212> TYPE: DNA
<213> ORGANISM: Homo sapiens
<220> FEATURE:
<221> NAME/KEY: primer_bind
<222> LOCATION: (1)..(23)
<223> OTHER INFORMATION: Cloning reverse primer of CACNA2D1 part 1

<400> SEQUENCE: 37
aaccattagg atcgattgca aag                                       23

<210> SEQ ID NO 38
<211> LENGTH: 25
<212> TYPE: DNA
<213> ORGANISM: Homo sapiens
<220> FEATURE:
<221> NAME/KEY: primer_bind
<222> LOCATION: (1)..(25)
<223> OTHER INFORMATION: Cloning forward primer of CACNA2D1 part 2

<400> SEQUENCE: 38
tgtgtacctg gatgcattgg aactg                                     25

<210> SEQ ID NO 39
<211> LENGTH: 24

```
<212> TYPE: DNA
<213> ORGANISM: Homo sapiens
<220> FEATURE:
<221> NAME/KEY: primer_bind
<222> LOCATION: (1)..(24)
<223> OTHER INFORMATION: Cloning reverse primer of CACNA2D1 part2

<400> SEQUENCE: 39
accatcatcc agaatcacac aatc                                        24

<210> SEQ ID NO 40
<211> LENGTH: 22
<212> TYPE: DNA
<213> ORGANISM: Homo sapiens
<220> FEATURE:
<221> NAME/KEY: primer_bind
<222> LOCATION: (1)..(22)
<223> OTHER INFORMATION: Cloning forward primer of CACNA2D1 part 3

<400> SEQUENCE: 40
agagacatat gaggacagct tc                                          22

<210> SEQ ID NO 41
<211> LENGTH: 57
<212> TYPE: DNA
<213> ORGANISM: Homo sapiens
<220> FEATURE:
<221> NAME/KEY: primer_bind
<222> LOCATION: (1)..(57)
<223> OTHER INFORMATION: Cloning reverse primer of CACNA2D1 part 3

<400> SEQUENCE: 41
gtcgactact tgtcatcgtc atccttgtaa tcctcgagta acaggcggtg tgtgctg    57

<210> SEQ ID NO 42
<211> LENGTH: 29
<212> TYPE: DNA
<213> ORGANISM: Homo sapiens
<220> FEATURE:
<221> NAME/KEY: misc_feature
<222> LOCATION: (1)..(29)
<223> OTHER INFORMATION: ShRNA sequence 1 corresponding to the
      nucleotides 546 to 574 in the coding sequence of CACNA2D1

<400> SEQUENCE: 42
actcaactgg acaagtgcct tagatgaag                                   29

<210> SEQ ID NO 43
<211> LENGTH: 29
<212> TYPE: DNA
<213> ORGANISM: Homo sapiens
<220> FEATURE:
<221> NAME/KEY: misc_feature
<222> LOCATION: (1)..(29)
<223> OTHER INFORMATION: shRNA2 sequence corresponding to the
      nucleotides 116 to 144 of the coding sequence of  CACNA2D1

<400> SEQUENCE: 43
agatgcaaga agaccttgtc acactggca                                   29
```